United States Patent
Khanna

(10) Patent No.: US 9,603,626 B2
(45) Date of Patent: Mar. 28, 2017

(54) TELESCOPIC CRANIAL BONE SCREW

(76) Inventor: Rohit Khanna, Daytona Beach, FL (US)

( * ) Notice: Subject to any disclaimer, the term of this patent is extended or adjusted under 35 U.S.C. 154(b) by 281 days.

(21) Appl. No.: 12/924,401

(22) Filed: Sep. 27, 2010

(65) Prior Publication Data

US 2012/0165879 A1    Jun. 28, 2012

Related U.S. Application Data

(60) Provisional application No. 61/246,137, filed on Sep. 27, 2009.

(51) Int. Cl.
| | | |
|---|---|---|
| A61B 17/80 | (2006.01) | |
| A61B 17/86 | (2006.01) | |
| A61B 17/88 | (2006.01) | |
| A61B 17/68 | (2006.01) | |
| A61B 17/00 | (2006.01) | |

(52) U.S. Cl.
CPC ........ *A61B 17/688* (2013.01); *A61B 17/8625* (2013.01); *A61B 17/8685* (2013.01); *A61B 2017/00004* (2013.01)

(58) Field of Classification Search
CPC ... A61B 17/685; A61B 17/686; A61B 17/688; A61B 17/86; A61B 17/8605; A61B 17/8625; A61B 17/864; A61B 17/8645; A61B 17/8665; A61B 17/8685; A61B 17/885; A61B 17/1695; A61B 2017/8655; A61B 2017/867; A61B 2017/8675; A61F 2/2875
USPC ............... 606/280, 281, 282, 286, 300–302, 606/304–310, 314, 320, 322–323, 326, 606/328–329, 902–903; 623/17.17–17.19, 23.47
See application file for complete search history.

(56) References Cited

U.S. PATENT DOCUMENTS

| | | | |
|---|---|---|---|
| 4,011,602 A * | 3/1977 | Rybicki et al. ............ | 623/23.76 |
| 5,578,036 A | 11/1996 | Stone et al. | |
| 5,707,373 A | 1/1998 | Sevrain et al. | |
| 5,800,436 A | 9/1998 | Lerch | |
| 5,902,304 A | 5/1999 | Walker et al. | |
| 5,916,200 A | 6/1999 | Eppley et al. | |
| 5,916,217 A | 6/1999 | Manthrop et al. | |
| 5,993,448 A | 11/1999 | Remmler | |
| 6,187,004 B1 | 2/2001 | Fearon | |
| 6,302,884 B1 * | 10/2001 | Wellisz et al. ............. | 606/86 B |
| 6,355,036 B1 | 3/2002 | Nakajima | |
| 6,379,363 B1 | 4/2002 | Herrington et al. | |
| 6,485,493 B1 | 11/2002 | Bremer | |
| 6,685,707 B2 | 2/2004 | Roman et al. | |
| 6,755,834 B2 | 6/2004 | Amis | |
| 7,048,737 B2 | 5/2006 | Wellisz et al. | |
| 7,387,633 B2 | 6/2008 | Ahmad et al. | |

(Continued)

FOREIGN PATENT DOCUMENTS

CH    WO 2009043827 A1 *    4/2009    .......... A61B 17/746

*Primary Examiner* — Kevin T Truong
*Assistant Examiner* — Tracy Kamikawa

(57) ABSTRACT

The invention provides a method and apparatus for cranial fixation following a craniotomy and treatment for increased intracranial pressure. The cranial fixation device comprises of plates attached to the skull with a telescopic screw. The telescopic screw provides constrained movement of the bone flap relative to the skull to accommodate an increase in the intracranial pressure.

12 Claims, 34 Drawing Sheets

(56) References Cited

U.S. PATENT DOCUMENTS

| | | | |
|---|---|---|---|
| 2007/0293865 A1* | 12/2007 | Ko | A61B 17/8061 606/916 |
| 2008/0027444 A1* | 1/2008 | Malek | A61B 17/686 606/86 A |
| 2008/0200954 A1* | 8/2008 | Tucci | 606/280 |
| 2010/0104999 A1* | 4/2010 | Bulloch | A61B 17/663 433/7 |

* cited by examiner

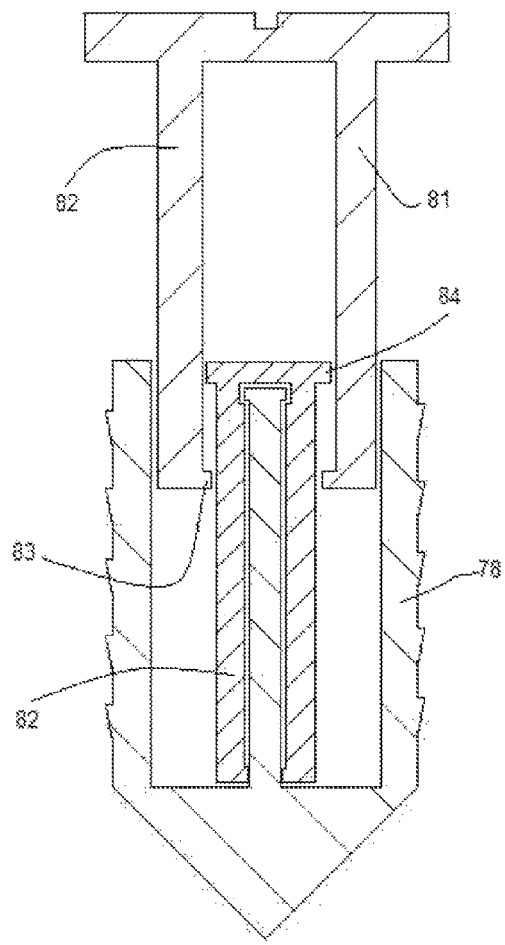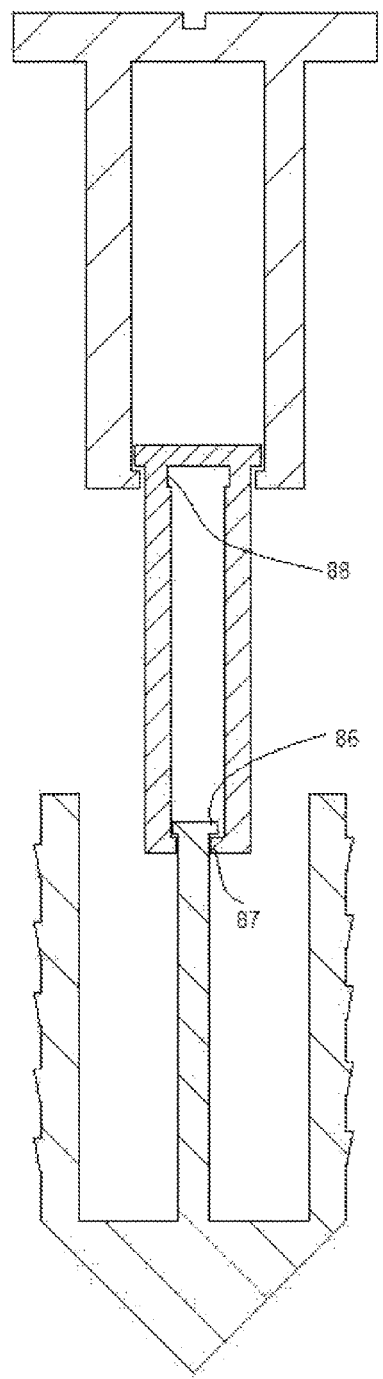
Fig.30
Fig.31

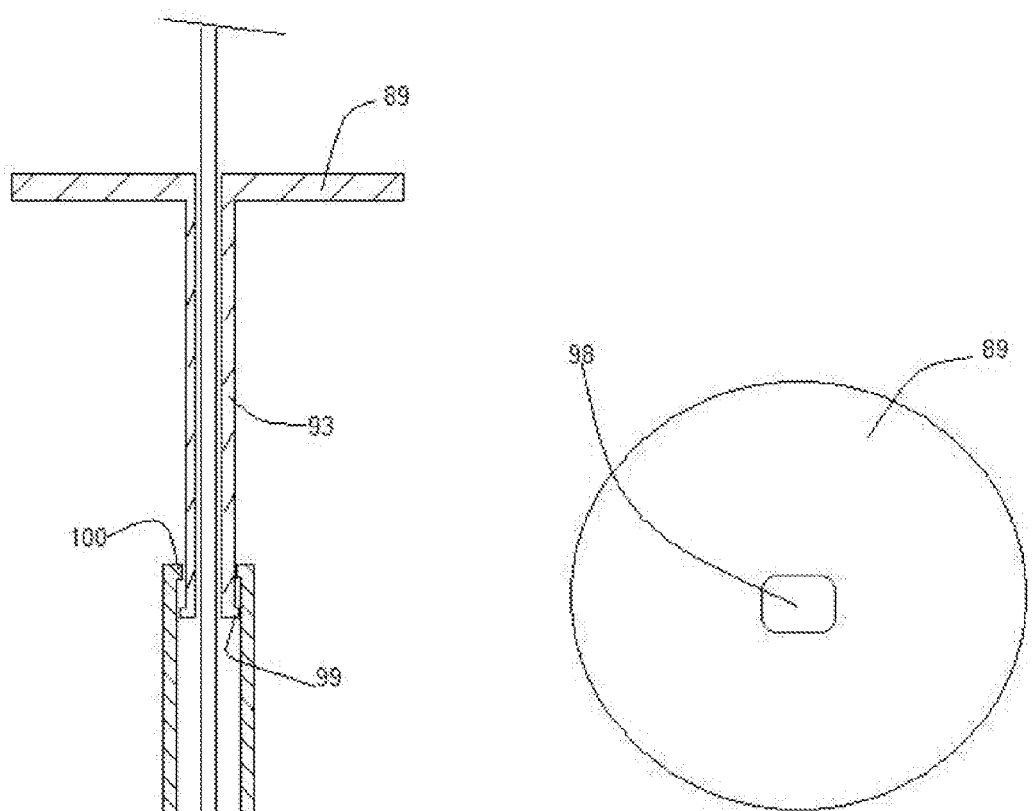
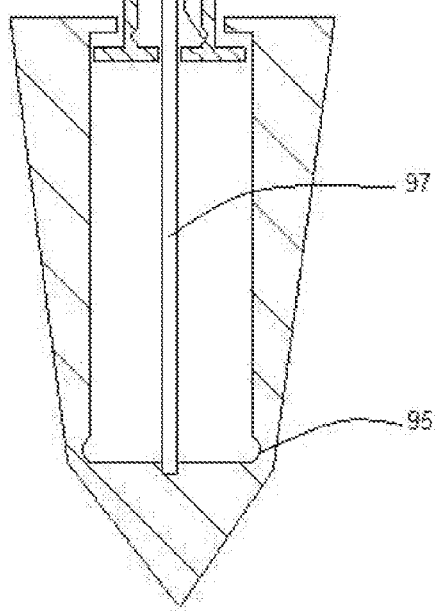
Fig.35
Fig.32

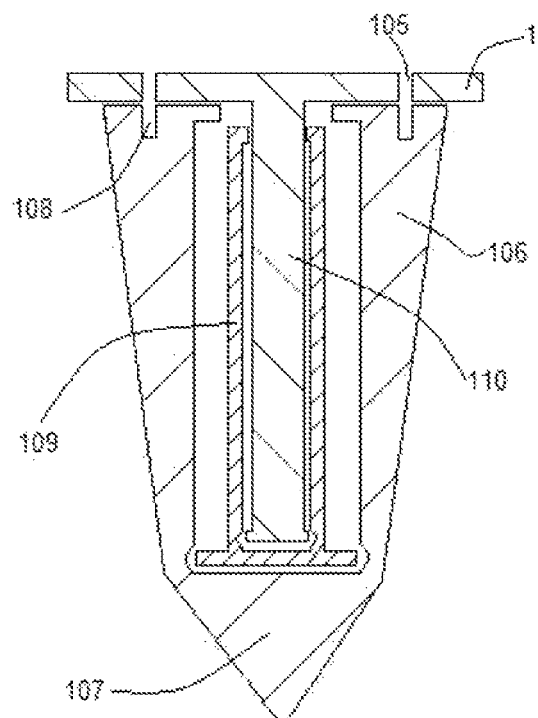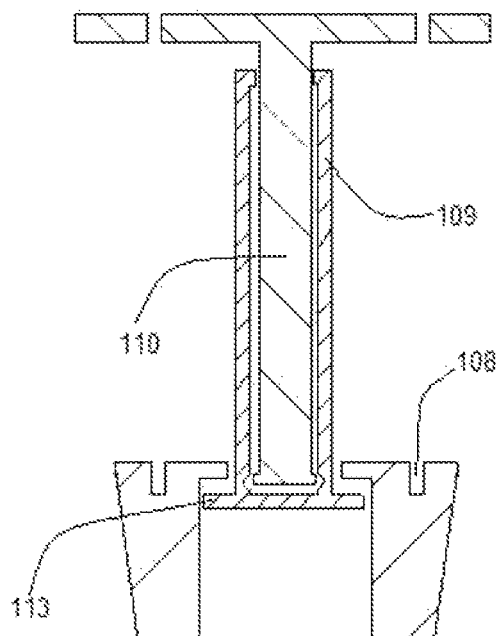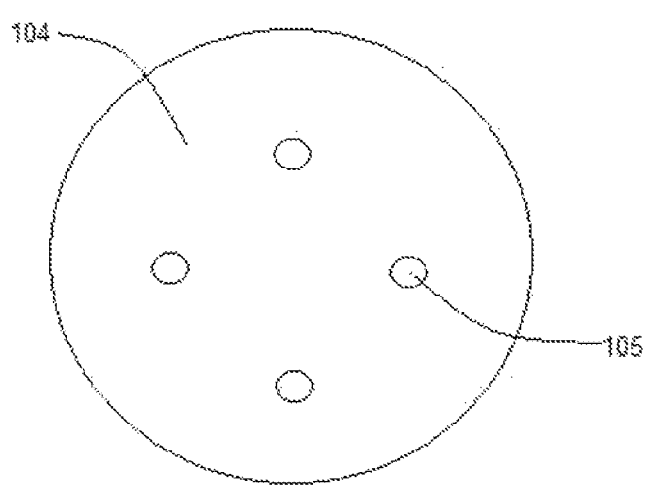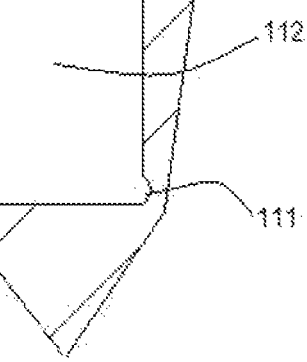
Fig.40
Fig.42
Fig.41

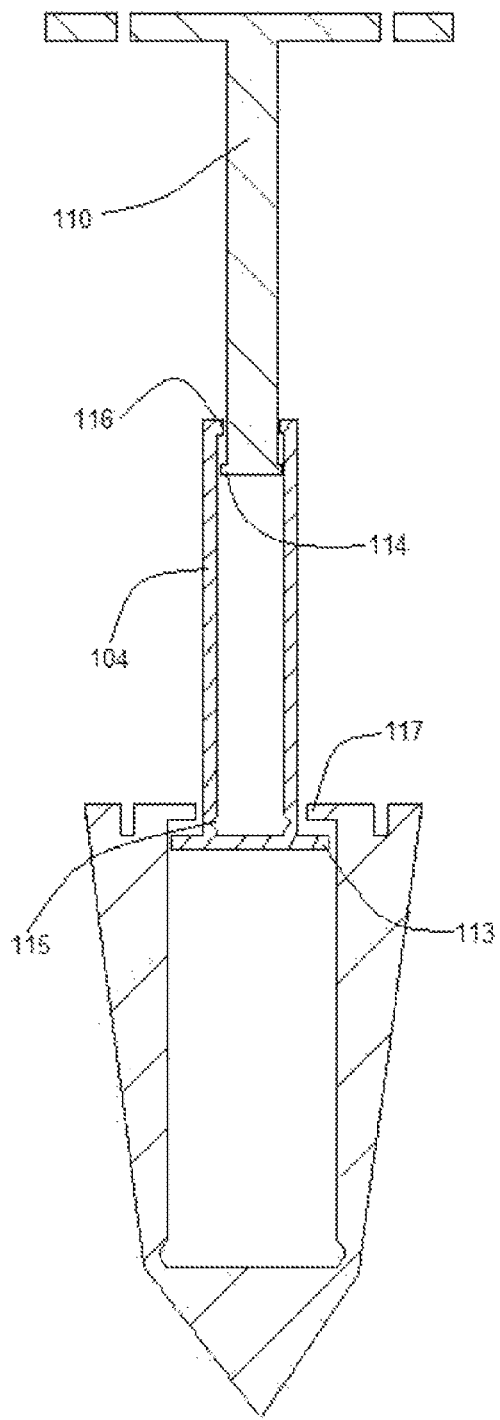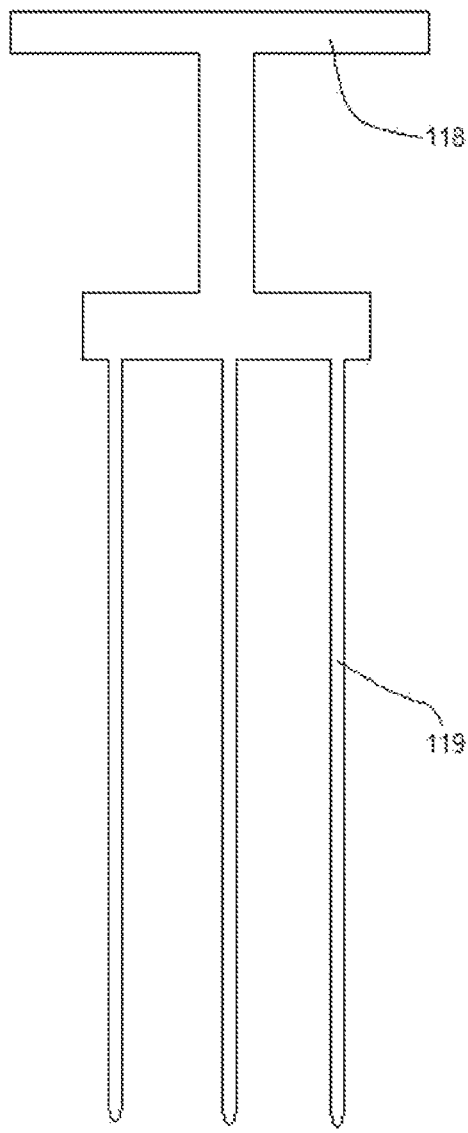
Fig.43
Fig.44

TELESCOPIC CRANIAL BONE SCREW

BACKGROUND OF THE INVENTION

Neurosurgery routinely involves performing craniotomies for exposure of the brain and intracranial contents for various intracranial pathologies including tumors, head injuries, vascular malformations, aneurysms, infections, hemorrhages, strokes, and brain swelling. A craniotomy involves creation of burr holes and removal of a portion of the skull (bone flap) with subsequent approximation of the bone flap for closure. Several methods and fixation devices are available for re-attaching the bone flap to the skull including small metallic or absorbable plates with screws or wires. Another method has been the use of cranial clamps consisting of two connected circular elements placed on the inside and outside surfaces of the skull. All of the aforementioned cranial fixation devices in the prior art provide for a rigid fixation of the bone flap to the skull.

In cases of post-operative intracranial hemorrhage and/or brain swelling development, a decompressive craniectomy is performed. Decompressive craniectomy is a neurosurgical procedure used to treat increased intracranial pressure (ICP) from head injury, stroke, brain tumor, infection, cerebral hemorrhage, and space occupying lesions. The technique involves removal of the skull and opening of the dura mater covering the brain, thereby allowing the swollen brain to herniate outwards through the surgical skull defect rather than downwards to compress the brainstem. The procedure improves outcomes by lowering ICP, the pressure within the skull. Increased ICP is very often debilitating or fatal because it causes compression of the brain and restricts cerebral blood flow. The aim of decompressive craniectomy is to reduce this pressure. The larger the removed bone-flap is, the more ICP is reduced. Following removal of the bone flap, the dural opening is closed with a patch graft taken from a cow, pig, cadaver, or a synthetic graft. The preferred method is a synthetic collagen matrix since it is capable of expanding. In addition to reducing ICP, studies have found decompressive craniectomy to improve cerebral perfusion pressure and cerebral blood flow in head injured patients.

Decompressive craniectomy is used to treat major strokes associated with malignant brain swelling and increased ICP. It is well known that a decompressive craniectomy improves survival and functional outcome in patients with severe brain swelling from head injury or stroke if performed in a timely manner. There usually is an inherent time delay between diagnosing the cause of the increased intracranial pressure and performing the decompressive craniectomy. Typically, once a post-operative increase in ICP is detected, either through a clinical exam or an ICP monitoring device, medical treatment is initiated and a CT or MRI imaging is obtained to identify the underlying cause of the raised intracranial pressure. If the need for a re-operation or decompressive craniectomy is identified, the anesthesiologist and operating room staff are notified and the surgery is subsequently undertaken. Unfortunately, at times the operating room and/or staff are at full capacity necessitating further delay until the surgery can be performed. Despite the best of attempts by the surgeon, in cases of massive brain swelling or a rapidly developing post-operative hemorrhage, the patient may end up with irreversible brainstem injury with consequent vegetative state or death.

After a craniectomy, the risk of brain injury is increased because of the removed bone flap, particularly after the patient heals and becomes mobile again. Therefore, special measures must be taken to protect the brain, such as a helmet or a temporary implant in the skull.

When the patient has healed sufficiently, the craniectomy skull defect is usually closed with a cranioplasty. Cranioplasty is repair of a defect in the vault of the skull. This repair can be carried out by using bone removed at earlier surgery that has been preserved or by using bone from elsewhere as a graft. The iliac bone bounding the pelvis, ribs and even a part of adjacent skull bone can be used. If possible, the original bone flap is preserved after the craniectomy in anticipation of the cranioplasty. The bone flap is usually stored sterilely in a freezer until the patient is ready for implantation of the bone flap into the craniectomy skull defect. Typically, this time period can last several months since it may take this long to treat the underlying cause of the increased intracranial pressure. This extended time period not only increases the risk of brain injury but also increases the risk of infection in the stored bone flap. Another technique of storing the removed bone flap involves placing it under the skin in the abdomen. This requires a surgical procedure to place the bone flap in the abdomen and another one to remove it, thereby also increasing the consequent risks to the patient. In cases where the bone flap cannot be replaced due to infection or any other reason, the skull defect is repaired either with a prosthetic plate or a titanium mesh and bone cement. A prosthesis obviously cannot completely replicate the original skull defect and therefore, some cosmetic deformity persists following a prosthetic cranioplasty. The prosthesis also increases the risk of infection.

The risks associated with cranioplasty include infection, hemorrhage, brain injury, seizures, and death along with other risks inherent to any surgery and general anesthesia. It is also usually necessary for the patient to be in hospital for a week or so after a cranioplasty.

U.S. Pat. No. 5,902,304 to Walker et al. describes a telescopic bone plate for use in bone lengthening by distraction osteogenesis. The bone plates are attached to osteomically separated mandible or skull sections connected by a thread screw assembly. The extent of the required distraction can be adjusted by an external screwdriver. U.S. Pat. No. 5,993,448 to Daniel J. Remmler describes a skull fixation device for treatment of craniofacial deformities that provides for relative movement of the skull segments by a percutaneously placed external wrench. U.S. Pat. No. 6,187,004 to Jeffrey A. Fearon describes a mandible or skull expansion plate. The extent of the expansion is adjusted by an externally placed device.

The aforementioned cranial fixation devices in the prior art provide for treatment of craniofacial defects in particular craniosynostosis. They all require an external screwdriver to control the extent of the skull movement allowed and they do not describe or provide for outward or inward movement of the both flap relative to the skull in response to a change in the intracranial pressure.

U.S. patent application No. 60/812,105 to Kathryn Ko describes a method of performing decompressive craniectomy with the bone flap attached to the skull with a hinged plate. The method describes attaching the hinged plate to one end of the bone flap and a rigid plate to the other end. The described method also requires a re-operation to fixate the unconstrained bone flap at the rigid plate end to the skull. U.S. patent application Ser. No. 12/033,815 to Tucci also describes a method similar to the Ko application of attaching the bone flap to the skull with a hinged plate at one end of the bone flap and a straight plate at the other end with unconstrained bone flap movement. They also describe a deformable plate which could be used instead of a hinged plate for bone flap attachment. This construct would also require a re-operation to fixate the unconstrained bone flap at the straight plate end. Tucci also describes a two part sliding device for cranial fixation. The device is not very practical as it very significantly sticks outwards from the skull surface and has a very high profile and obvious painful cosmetic defect with overlying skin irritation and risk of erosion/infection. This device would also require another operation to remove it once the bone flap approximates to the skull.

Considering the aforementioned complexities and risks involved in the post-operative management of critically ill patients undergoing a craniotomy, there is a need for a better technique which provides for cranial fixation along with immediate treatment of increased intracranial pressure and avoids the need for performing a subsequent cranioplasty.

SUMMARY OF THE INVENTION

The present invention relates to a cranial fixation device for fixing a bone flap to the skull following a craniotomy. It also provides for constrained outward movement of the bone flap to immediately accommodate for an increase in intracranial pressure and subsequently allowing for the bone flap to move inwards up to the skull once the intracranial pressure normalizes.

In one embodiment, the cranial fixation device comprises of a plate that attaches to the skull and bone flap. The plates are attached to the skull with telescopic screws and the bone flap with regular screws. The telescopic screws allow outward movement of the bone flap as well as inward movement of the bone flap up to the skull level. The plate does not allow the bone flap to move inward inside the cranium below the skull level.

In another embodiment, the cranial fixation device comprises a plate that attaches to the skull and bone flap with bone fasteners. The bone fasteners attached to the skull are telescopic and bone fasteners attached to the bone flap are regular screws. The telescopic bone fasteners also comprise a locking mechanism that engages when the telescopic bone fastener is in a retracted position. The retracted telescopic bone position approximates the bone flap to the skull when the intracranial pressure is in the normal range. With an increase in ICP, the pressure placed on the bone flap disengages the telescopic bone fastener locking mechanism and allows outward movement of the bone flap to accommodate the increase in ICP and subsequently allowing the bone flap to retract back to the skull level once the ICP normalizes. The telescopic screw locking mechanism comprises of one or more collapsible balls mounted on one telescopic extension with corresponding sockets on the said second telescopic component. Other locking mechanisms include ratchet teeth, ratchet teeth and pawl mechanism, collapsible ratchet teeth, threads, and ridges with notches. Several locking mechanisms are described here forth. In one embodiment of the telescopic screw, the locking mechanism comprises a ridge in the telescopic extension with a corresponding socket along the axial and longitudinal axis of the screw wall. In another embodiment of the telescopic screw, the locking mechanism comprises of ridges in the telescopic extension with notches in the inner screw wall. In another embodiment of the telescopic screw, the locking mechanism comprises of ratchet teeth in the telescopic extension and inner screw wall. In another embodiment of the telescopic screw, the locking mechanism comprises of ratchet teeth in the telescopic extension with a pawl in the inner screw wall. The ratchet teeth can be unidirectional or bidirectional. In another embodiment of the telescopic screw, the locking mechanism comprises of collapsible ratchet teeth in the telescopic extension with an engaging defect or ratchet teeth in the inner screw wall. In another embodiment of the telescopic screw, the locking mechanism comprises of threads in the telescopic extension and the inner screw wall. In another embodiment of the telescopic screw, the locking mechanism comprises of a spring. The spring loaded telescopic screw places the screw in a retracted position once the intracranial pressure normalizes and positions the bone flap in proximity to the skull.

Rather than providing a fixed locked position once implanted as described in all the cranial fixation devices in the prior art, the current invention allows for constrained outward movement of the bone flap relative to the skull in cases of cerebral swelling and subsequently retracts the bone flap against the skull once the swelling subsides.

In the various embodiments described herein the preferred plate configuration is circular so as to cover the burr hole or skull opening. Other plate configurations could be rectangular, square, straight, X-shaped, Y-shaped, fan shaped, or any other configuration able to connect the skull to the bone flap. Similarly, the telescopic configurations described are either cylindrical or rectangular and designed to fit into the hollow screw. Other telescopic configurations could be partially solid, tapered, V-shaped or any other configuration that fit's the screw opening. The plate and screws can be made of titanium or titanium alloy for MRI imaging compatibility. They could also be made of a bio-absorbable material (polyesters, poly amino acids, polyanhydrides, polyorthoesters, polyurethanes, polycarbonates, homopolymers, copolymers of poly lactic acid and poly glycolic acid, copolyesters of e-caprolactone, trimethylene carbonate, and para-dioxanone), or allograft or xenograft bone that is absorbed by the body over time once the bone flap has fused with the skull. Alternatively, it could made of a radiolucent material (polyetheretherketone), plastic, or a combination of plastic and metal to reduce CT and MRI imaging artifact.

Although the application for the cranial fixation device described in the various embodiments is for fixation of the bone flap to the skull following a craniotomy, it can also be used to cover a burr hole or skull fracture. Other applications include treatment of increased intracranial pressure following traumatic injury, subdural hemorrhage, epidural hemorrhage, subarachnoid hemorrhage, intra-ventricular hemorrhage, brain hemorrhage, ischemic stroke, hemorrhagic stroke, hypoxia, tumor, infection, brain swelling, and/or seizure. The plate and screw construct not only approximate the bone flap to the skull but can also allow external movement of the bone flap relative to the skull in case of an increased intracranial pressure. The external movement of the bone flap increases the intracranial space to accommodate the increase in intracranial pressure and provides for a decompressive craniectomy. Following normalization of the intracranial pressure, the bone flap retracts back towards the skull.

BRIEF DESCRIPTION OF THE DRAWINGS

FIG. 15 FIG. 11 is a cross-sectional side view of another embodiment of the telescopic screw in a retracted position.

FIG. 30 is a cross-sectional side view of the screw in FIG. 29 shown in a partially extended position.

FIG. 31 is a cross-sectional side view of the screw in FIG. 29 shown in a completely extended position.

FIG. 32 is a top view of another embodiment of the screw head.

FIG. 35 is a cross-sectional side view of the screw in FIG. 33 shown in a completely extended position.

FIG. 40 is a cross-sectional side view of another embodiment of the telescopic screw in a retracted position.

FIG. 41 is a top view of the screw shown in FIG. 40

FIG. 42 is a cross-sectional side view of the screw in FIG. 40 shown in a partially extended position.

FIG. 43 is a cross-sectional side view of the screw in FIG. 40 shown in a completely extended position.

FIG. 44 is a side view of the screw driver used for placement of the screw shown in FIG. 40.

DETAILED DESCRIPTION OF THE PREFERRED EMBODIMENTS

Figure 1:
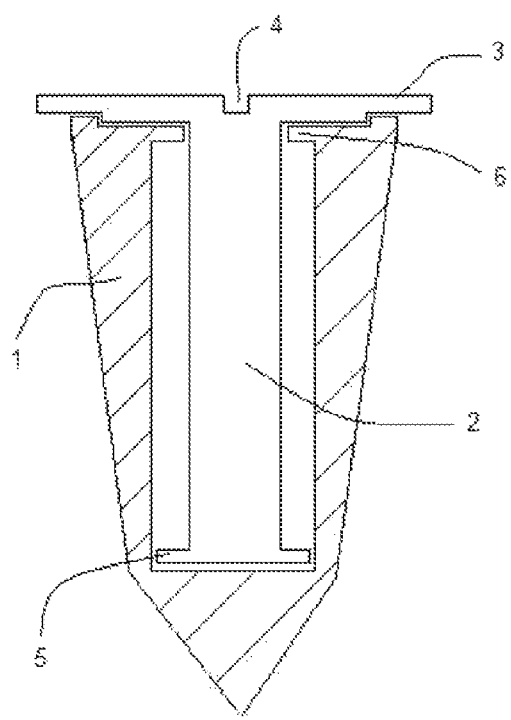
FIG. 1 is a cross-sectional side view of one embodiment of the telescopic screw in a retracted position.
Figure 2:
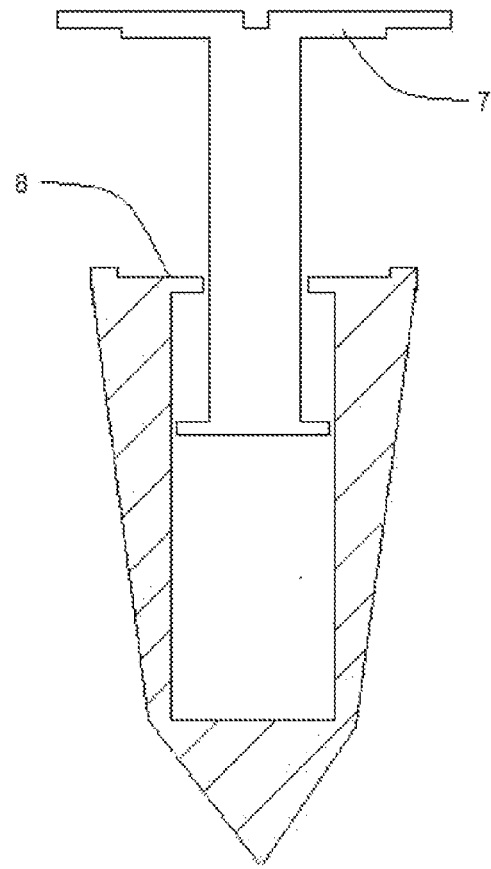
FIG. 2 is a cross-sectional side view of the screw in FIG. 1 shown in an extended position.

FIGS. 1 and 2 illustrate a telescopic screw with a housing component 1 and a telescopic component 2. The telescopic component at one end has a head with a recess 4 and a widened portion 3 and at the other end has extensions 5. The telescopic component 2 is contained inside the housing component 1. The housing component has extensions 6 and a recess 8. The screw is drilled into the skull with a screwdriver attached to the recess 4. FIG. 1 illustrates the telescopic screw in a retracted position with the wider head portion 3 engaged with the recess 8 to provide a locking mechanism. FIG. 2 illustrates the screw placed in an extended position by an increase in the intracranial pressure. The telescopic component extension 5 and the housing component extension 6 prevent the telescopic component from pulling out from the housing component during a maximally extended position.

Figure 3:
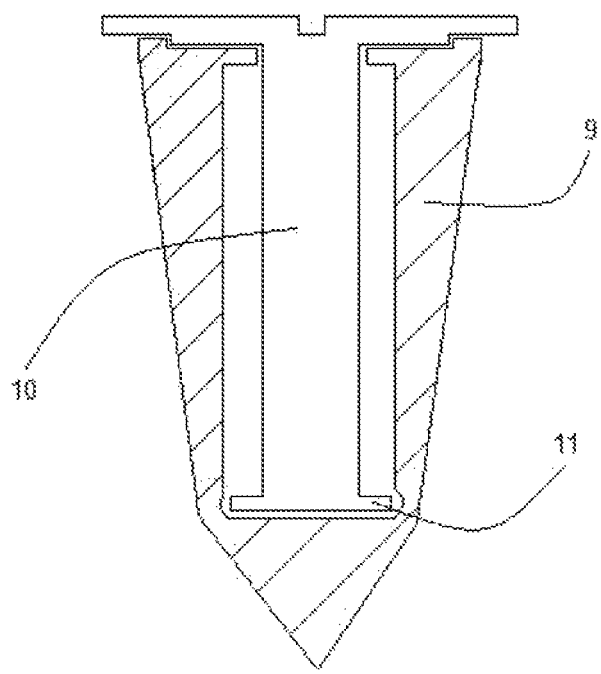
FIG. 3 is a cross-sectional side view of another embodiment of the telescopic screw in a retracted position.
Figure 4:
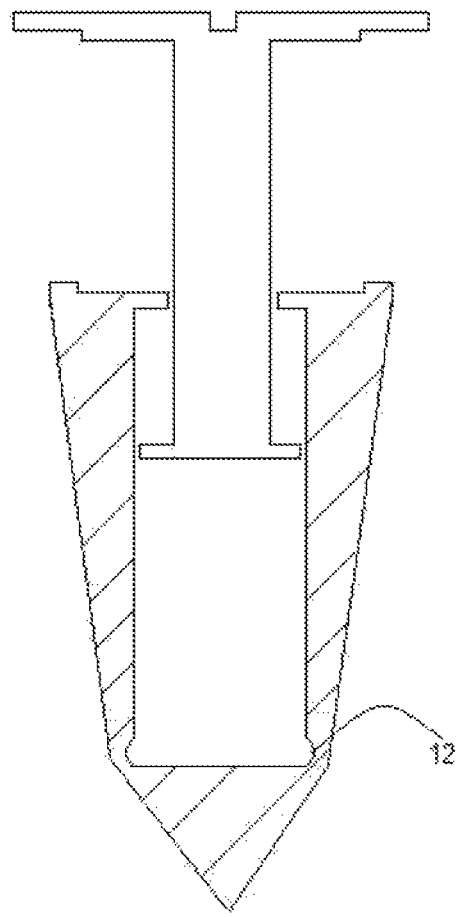
FIG. 4 is a cross-sectional side view of the screw in FIG. 3 shown in an extended position.

FIGS. 3 and 4 illustrate another embodiment of the telescopic screw. The telescopic component 10 has an extension 11 and the housing component 9 has a recess 12 at the screw tip end. As shown in FIG. 3 with the screw in a retracted position, the extension 11 and recess 12 are engaged and provide a locking mechanism. FIG. 4 illustrates the screw in an extended position.

Figure 5:
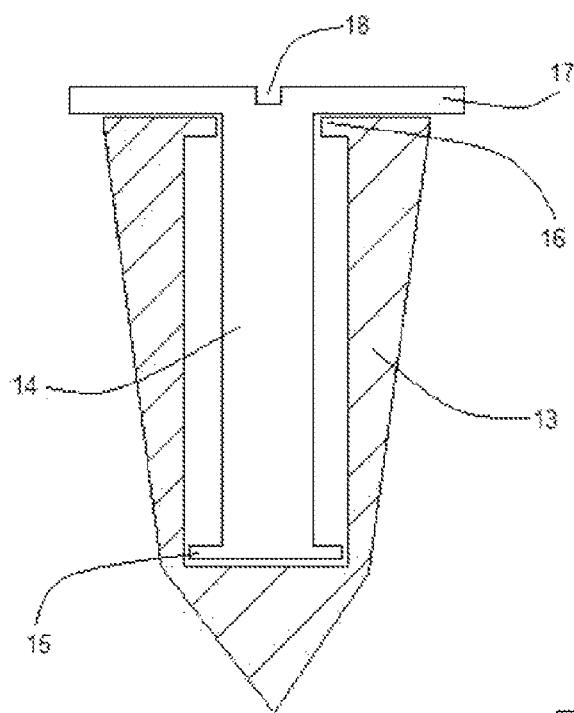
FIG. 5 is a cross-sectional side view of another embodiment of the telescopic screw in a retracted position.
Figure 6:
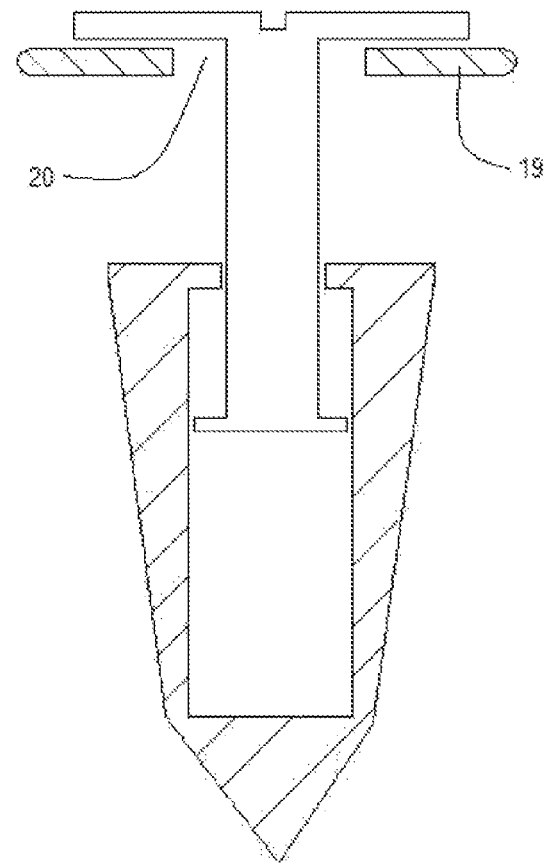
FIG. 6 is a cross-sectional side view of the screw in FIG. 5 shown in an extended position along with the plate.
Figure 7:
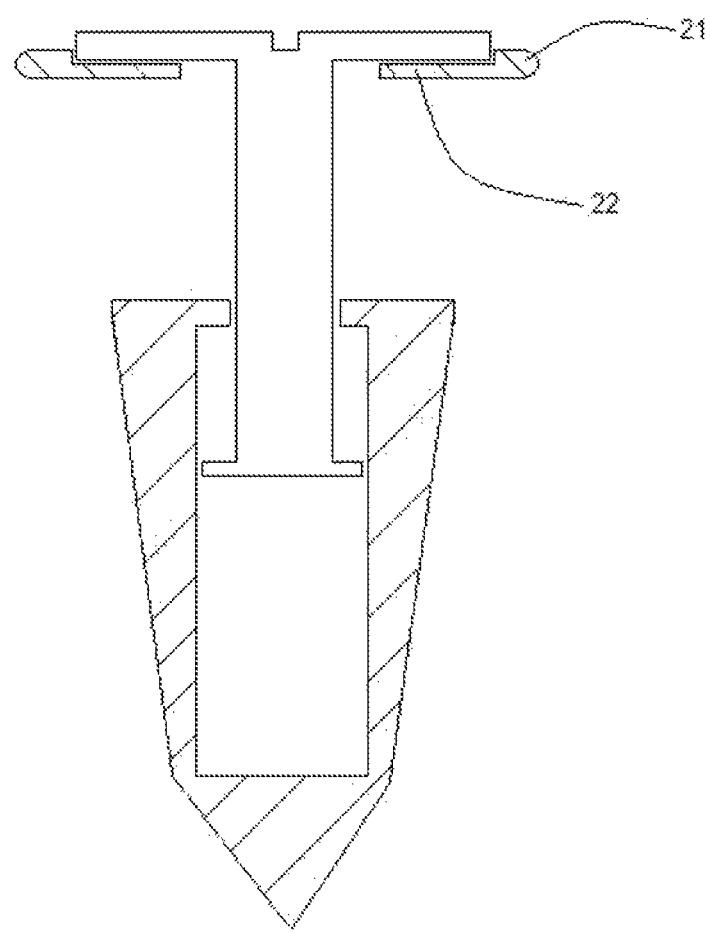
FIG. 7 is a cross-sectional side view of the screw seen in FIG. 6 with another embodiment of the plate.

FIGS. 5-7 illustrate another embodiment of the telescopic screw with a housing component 13 and a telescopic component 14. The telescopic component at one end has a head 17 with a recess 18 and at the other end has extensions 15. The telescopic component 14 is contained inside the housing component 13. The screw is drilled into the skull with a screwdriver attached to the recess 18. FIG. 5 illustrates the telescopic screw in a retracted position and FIG. 6 illustrates the screw placed in an extended position by the plate 19. The screw is placed through the plate hole 20. The plate 19 is attached to the skull and bone flap and a rise in the intracranial pressure forces the plate to move outwards with the bone flap, thereby placing the telescopic screw in an extended position. FIG. 7 illustrates the plate 21 with a recess 22 which provides a lower profile for the screw head and decreases the overlying skin irritation.

Figure 8:
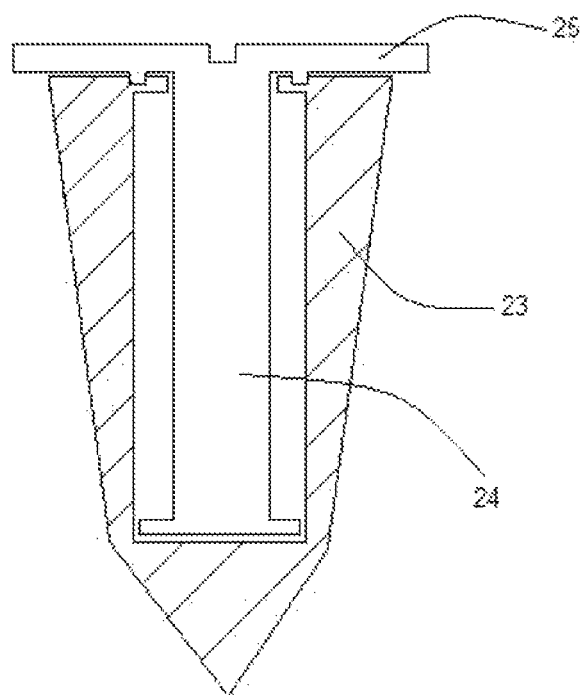
FIG. 8 is a cross-sectional side view of another embodiment of the telescopic screw in a retracted position.
Figure 9:
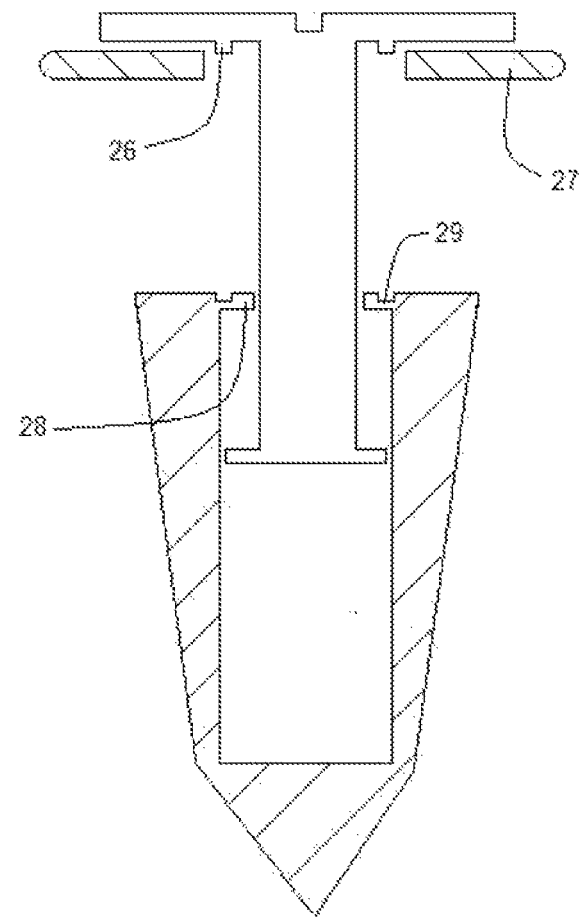
FIG. 9 is a cross-sectional side view of the screw in FIG. 8 shown in an extended position along with the plate.
Figure 10:
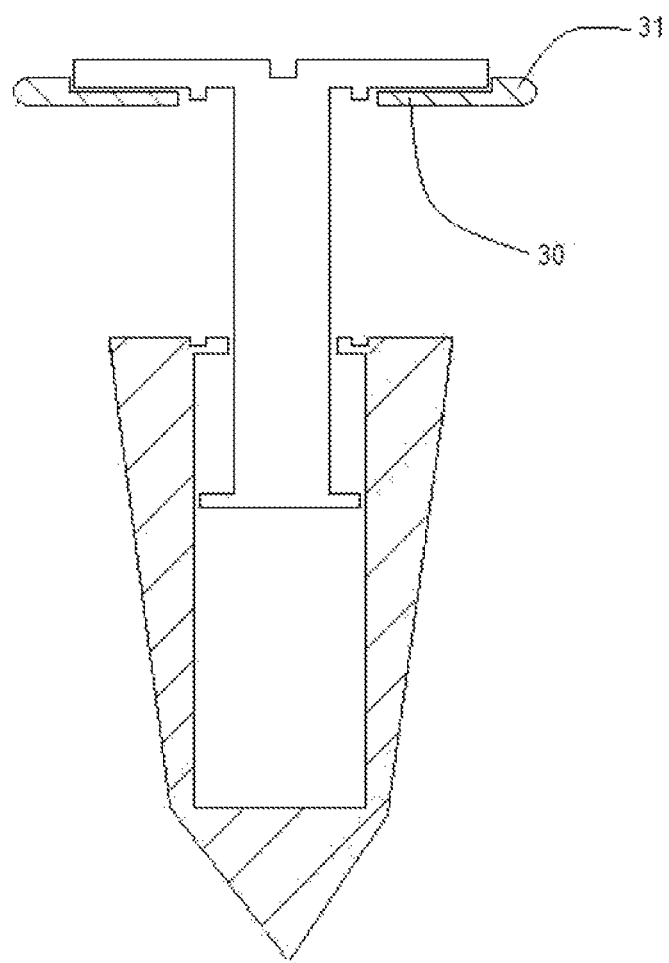
FIG. 10 is a cross-sectional side view of the screw seen in FIG. 9 with another embodiment of the plate.

FIGS. 8-10 illustrate another embodiment of the telescopic screw with a housing component 23 and a telescopic component 24. The telescopic component at one end has a head 25 and extensions 26. The housing component has extensions 28 and recess 29. In a retracted position as shown in FIG. 8, the head extension 26 engages with the housing component recess 29. FIG. 9 illustrates with screw in an extended position with the plate 27 and FIG. 10 illustrates the screw in an extended position with a lower profile plate 31 with a thinner screw head engaging portion 30.

Figure 11:
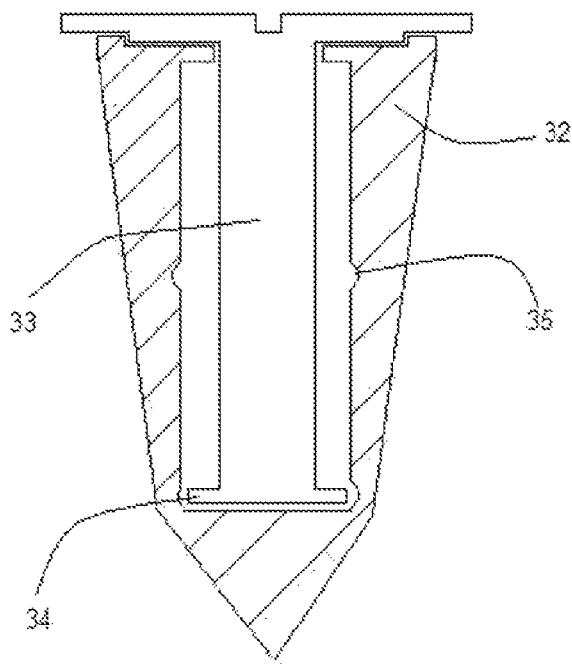
FIG. 11 is a cross-sectional side view of another embodiment of the telescopic screw in a retracted position.
Figure 12:
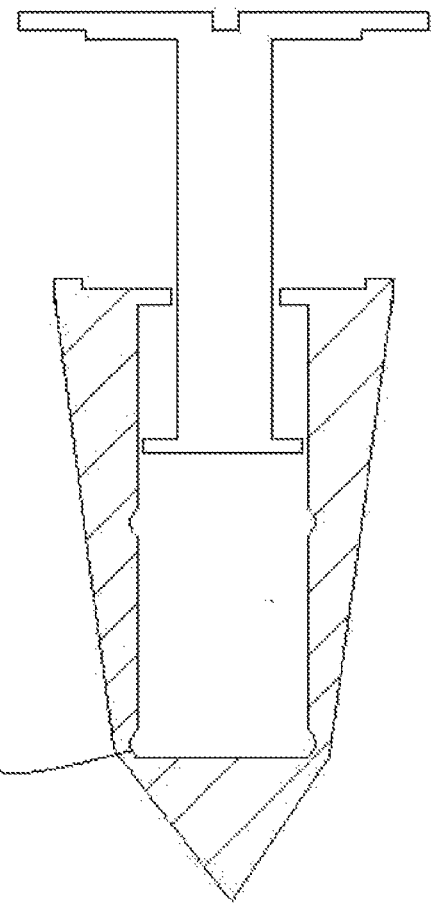
FIG. 12 is a cross-sectional side view of the screw in FIG. 11 shown in an extended position.

FIGS. 11 and 12 illustrate another embodiment of the locking mechanism for the telescopic screw with a housing component 32 and a telescopic component 33. The housing component comprises recesses 35 and 36 that engage with the extension 34 of the telescopic component 33. FIG. 11 shows the screw in a retracted position with the extension 34 engaged with the recess 36 and FIG. 12 illustrates an extended position of the screw.

Figure 13:
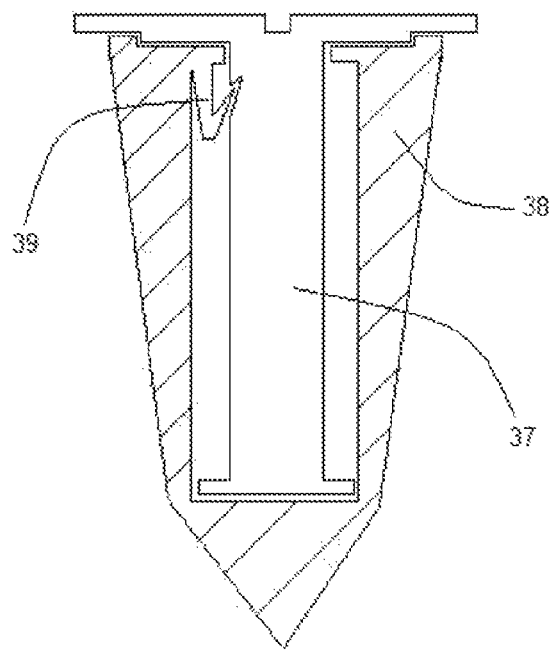
FIG. 13 is a cross-sectional side view of another embodiment of the telescopic screw in a retracted position.
Figure 14:
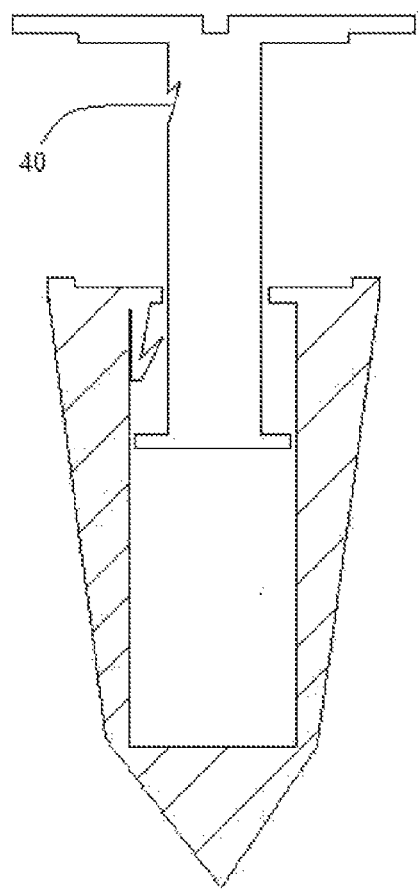
FIG. 14 is a cross-sectional side view of the screw in FIG. 13 shown in an extended position.

FIGS. 13 and 14 illustrate another embodiment of the locking mechanism for the telescopic screw. The housing component 38 contains a collapsible ratchet 39 that engages with the recess 40 in the telescopic component 37. FIG. 13 shows the screw in a retracted position with the ratchet tooth 39 engaged with the recess 40 and FIG. 14 shows the telescopic component in an extended position with the ratchet 39 collapsed back towards the housing component wall 38.

Figure 15:
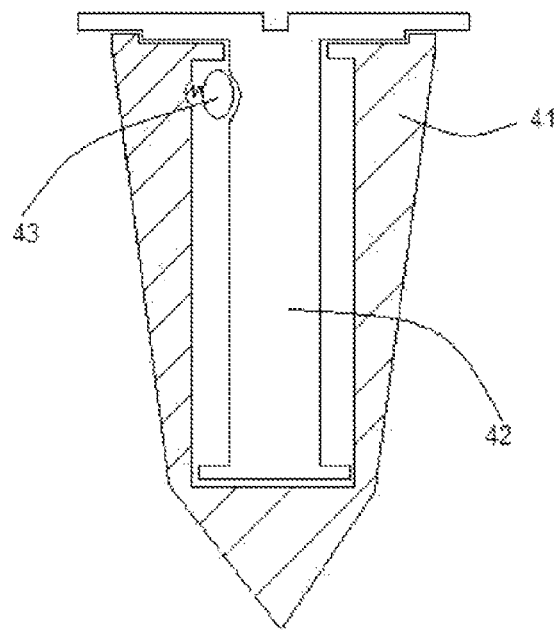
Figure 16:
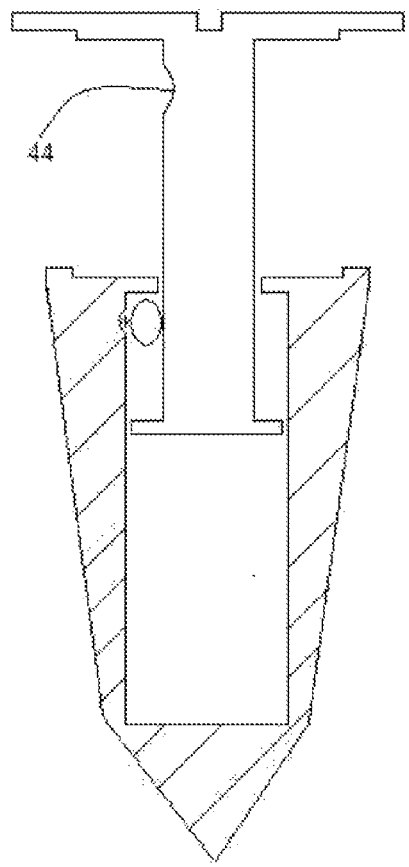
FIG. 16 is a cross-sectional side view of the screw in FIG. 15 shown in an extended position.

FIGS. 15 and 16 illustrate another embodiment of the locking mechanism for the telescopic screw. The housing component 41 contains a collapsible ball/spring 43 near the head of the screw that engages with the recess 44 on the telescopic component 42. FIG. 15 shows the screw in a retracted position with the ball 43 engaged with the recess 44 and FIG. 16 illustrates the screw in an extended position. In other embodiments the telescopic components can contain recesses in partially and completely extended screw positions also.

Figure 17:
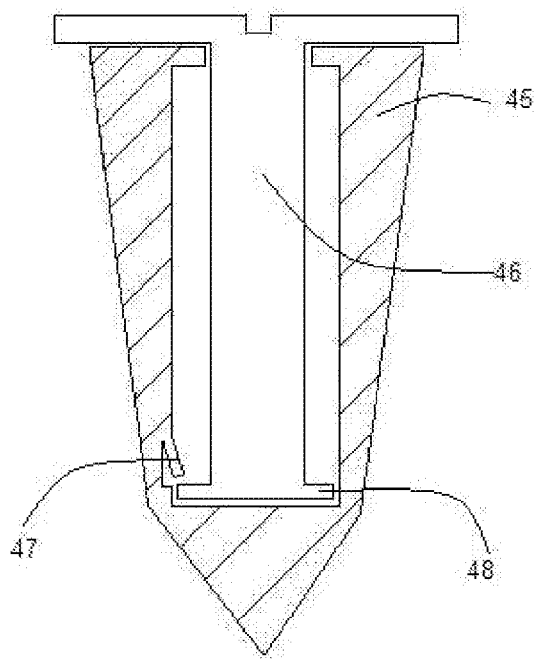
FIG. 17 is a cross-sectional side view of another embodiment of the telescopic screw in a retracted position.
Figure 18:
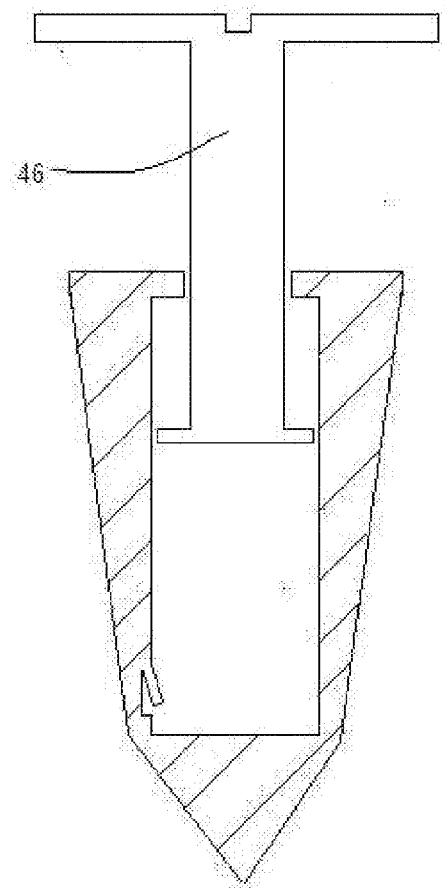
FIG. 18 is a cross-sectional side view of the screw in FIG. 17 shown in an extended position.

FIGS. 17 and 18 illustrate another embodiment of the locking mechanism for the telescopic screw. The housing component contains a collapsible extension 47. The telescopic component 46 contains an extension 48 which engages with extension 47 and locks the telescopic component in the retracted position. FIG. 18 shows the locking mechanism disengaged with the screw in an extended position.

Figure 19:
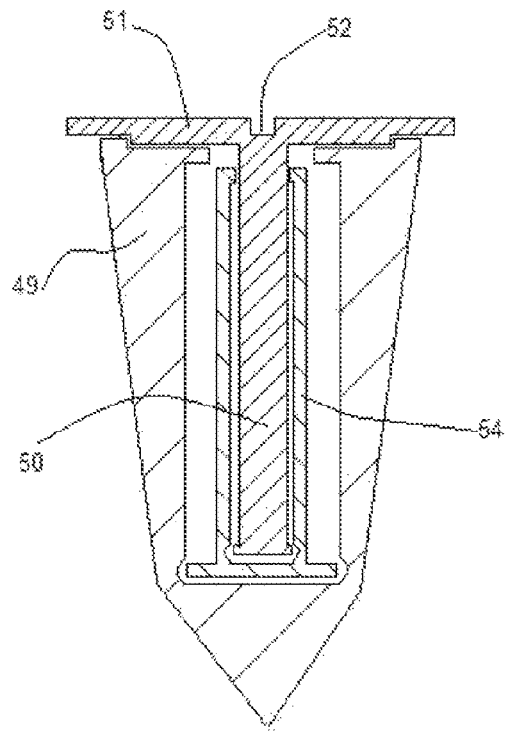
FIG. 19 is a cross-sectional side view of another embodiment of the telescopic screw in a retracted position.
Figure 20:
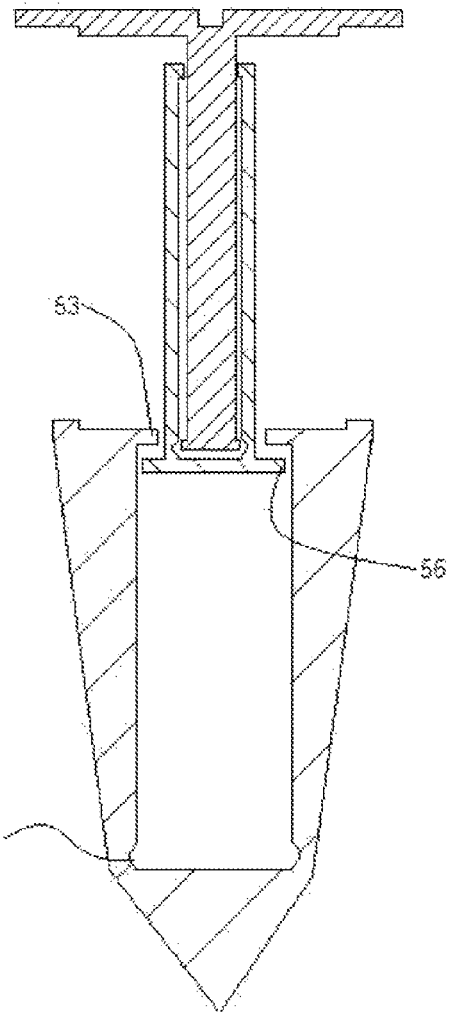
FIG. 20 is a cross-sectional side view of the screw in FIG. 19 shown in a partially extended position.
Figure 21:
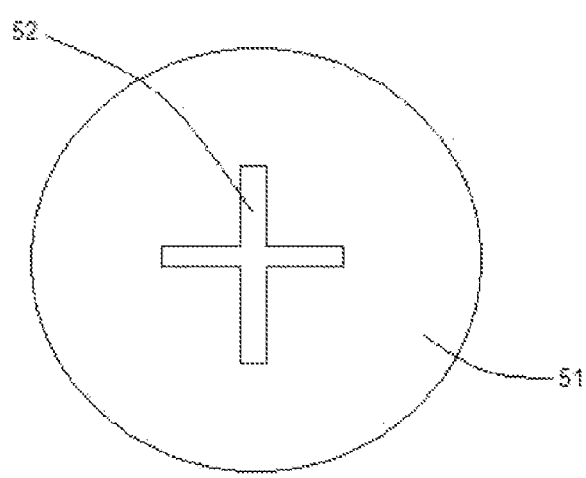
FIG. 21 is a top view of the screw head.
Figure 22:
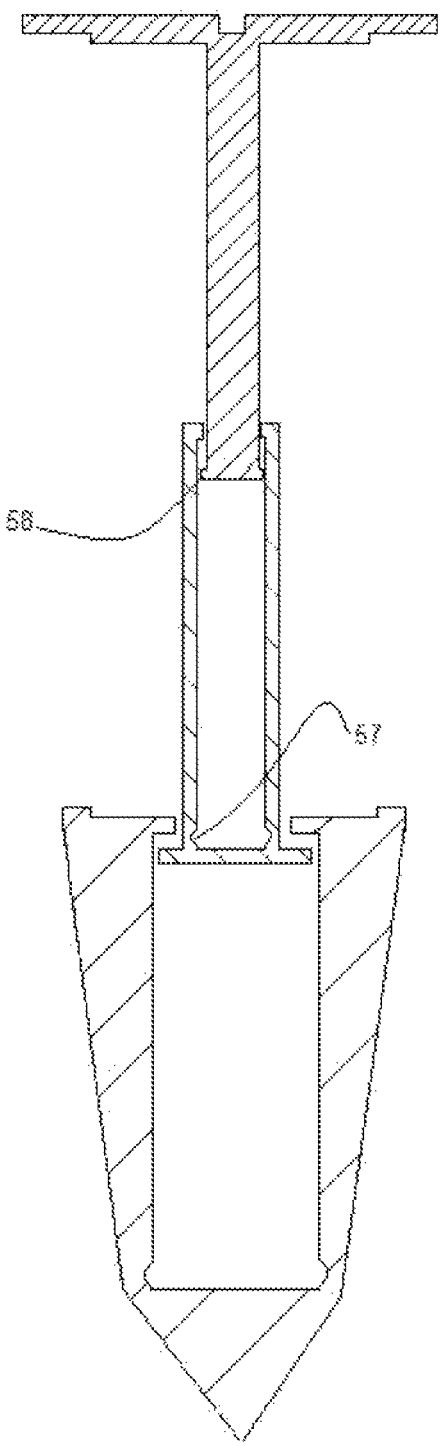
FIG. 22 is a cross-sectional view of the screw in FIG. 19 shown in a completely extended position.

FIGS. 19-22 illustrate another embodiment of the telescopic screw containing a housing component 49, a telescopic component 50 with a head 51 and an intermediate telescopic component 54. The head 51 contains a recess 52 for the screw driver at one end and an extension 58 at the other end. The intermediate telescopic component contains an extension 56 on the outside and a recess 57 inside. The housing component comprises of an extension 53 which engages with the extension 56 and prevents the intermediate extension from pulling out in an extended position as shown in FIG. 20. FIG. 19 illustrates the retracted position of the screw with telescopic portion 50 extension 58 engaged with the recess 57 in the intermediate portion 54 and the intermediate portion extension 56 engaged with the recess 55 in the housing component. FIG. 20 illustrates the partially extended position of the screw. FIG. 21 shows the top view of the screw head 51 with a recess 52 for the screwdriver. FIG. 22 illustrates the screw in a completely extended position.

Figure 23:
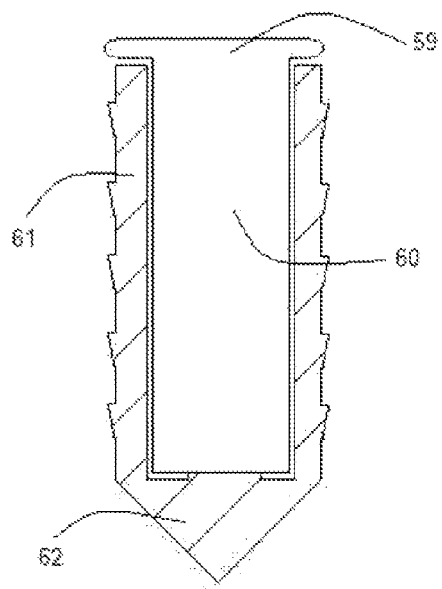
FIG. 23 is a cross-sectional side view of another embodiment of the telescopic screw in a retracted position.
Figure 25:
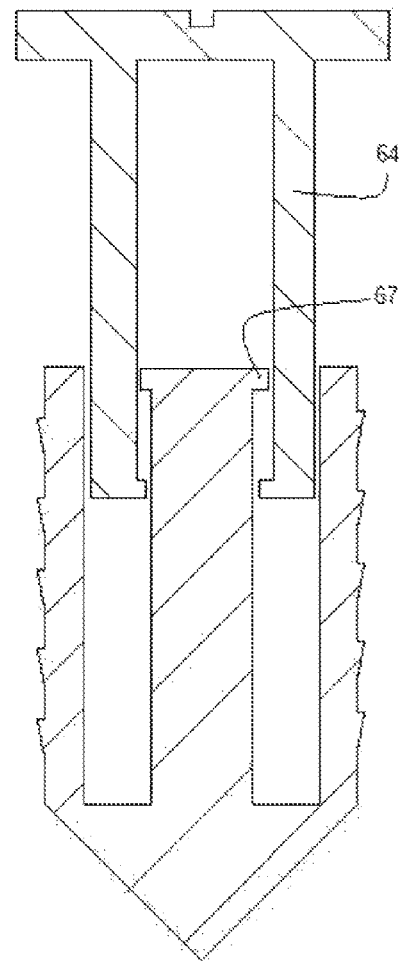
FIG. 25 is a cross-sectional side view of the screw in FIG. 24 shown in an extended position.
Figure 24:
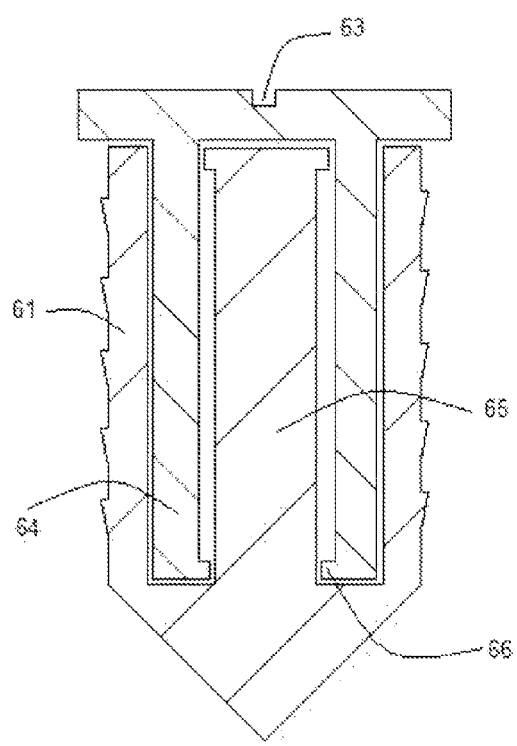
FIG. 24 is another cross-sectional side view of the screw in FIG. 23.

FIGS. 23-25 illustrate another embodiment of the telescopic screw with a housing component 61 with a screw head 62 and a telescopic component 60 and a head 59. The housing component 61 contains a central portion 65 with an extension 67. The telescopic component contains arms 64 with extensions 66 at the ends. The telescopic portion head 59 also contains a recess 63 for the screwdriver. FIGS. 23 and 24 illustrate the screw in a retracted position and FIG. 25 shows the screw in an extended position. The extension 67 engages with the extension 66 and prevents the telescopic component 64 from pulling out from the housing component 61.

Figure 26:
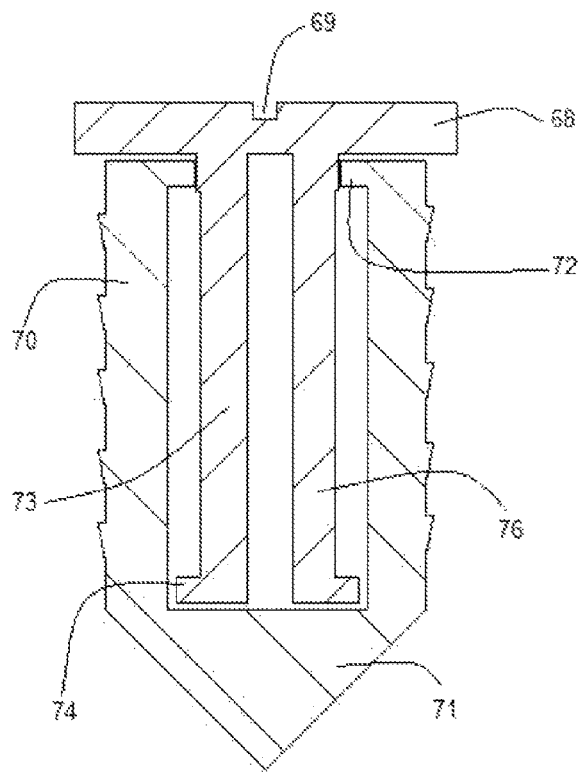
FIG. 26 is a cross-sectional side view of another embodiment of the telescopic screw in a retracted position.
Figure 27:
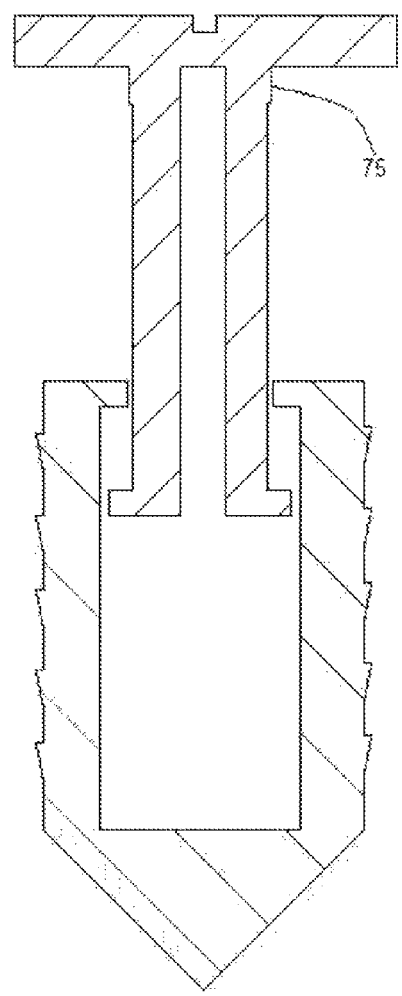
FIG. 27 is a cross-sectional side view of the screw in FIG. 26 shown in an extended position.

FIGS. 26 and 27 illustrate another embodiment of the screw with a telescopic component with a head 68 and extension arms 73 and 76 which each contain a wider portion 75 at the proximal end and an extension 74 at the distal end. The housing component 70 contains the screw tip 71 at one end and extensions 72 at the other end. The telescopic screw head 68 contains a recess 69 for the screwdriver. The wider portion 75 of the telescopic component arms engages with the extension 72 on the housing component and locks the screw in a retracted position as illustrated in FIG. 26. FIG. 27 illustrates the screw in an extended position. In other embodiments the telescopic component arms 73 and 76 can be manually compressed against each other and placed after the housing component is implanted into the skull bone.

Figure 28:
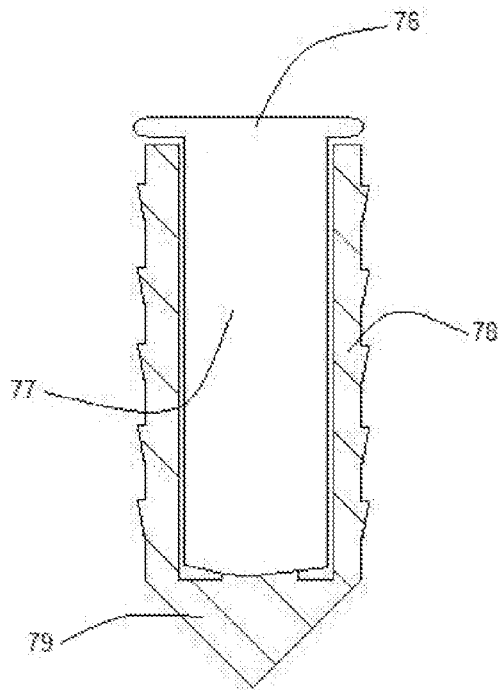
FIG. 28 is a cross-sectional side view of another embodiment of the telescopic screw in a retracted position.
Figure 29:
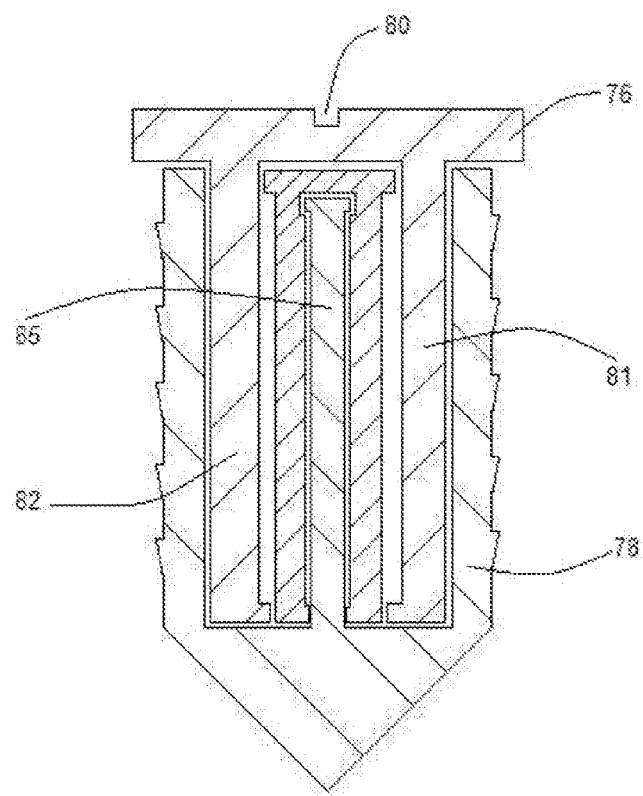
FIG. 29 is another cross-sectional side view of the screw in FIG. 28.

FIGS. 28-31 illustrate another embodiment of the telescopic screw with a housing component 78 with screw tip 79 and a telescopic component with a head 76 and body 77 as shown in FIG. 28. The telescopic component contains extension arms 81 with extension 83 at the distal end of the arms. The housing member also contains a central extension 85 with a widened tip 86. The screw also contains an intermediate telescopic component 82 with a head extension 84 at one end on the outside and a recess 88 on the inside as well as an extension 87 at the other end. FIG. 29 shows the screw in a retracted position. FIG. 30 shows the screw in a partially extended position with the telescopic component 81 in an extended position and intermediate component 82 in a retracted position. The extension 83 engages with the head 84 and prevents the telescopic component 81 from pulling out. The housing component central extension 85 widened tip 86 engages with the recess 88 in the intermediate telescopic component 82 during the retracted position. FIG. 31 illustrates the screw in a completely extended position. The telescopic component 81 extensions 83 engage with the intermediate component 82 head 84 and the housing component extension 85 widened tip 86 engages with the intermediate component extensions 87 and prevent the telescopic components from pulling out of the housing component in a completely extended screw position.

Figure 33:
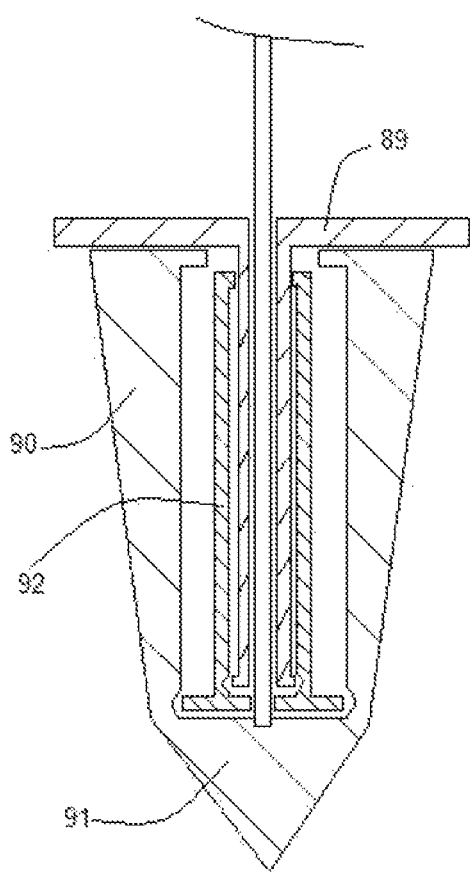
FIG. 33 is a cross-sectional side view of another embodiment of the telescopic screw in a retracted position.
Figure 34:
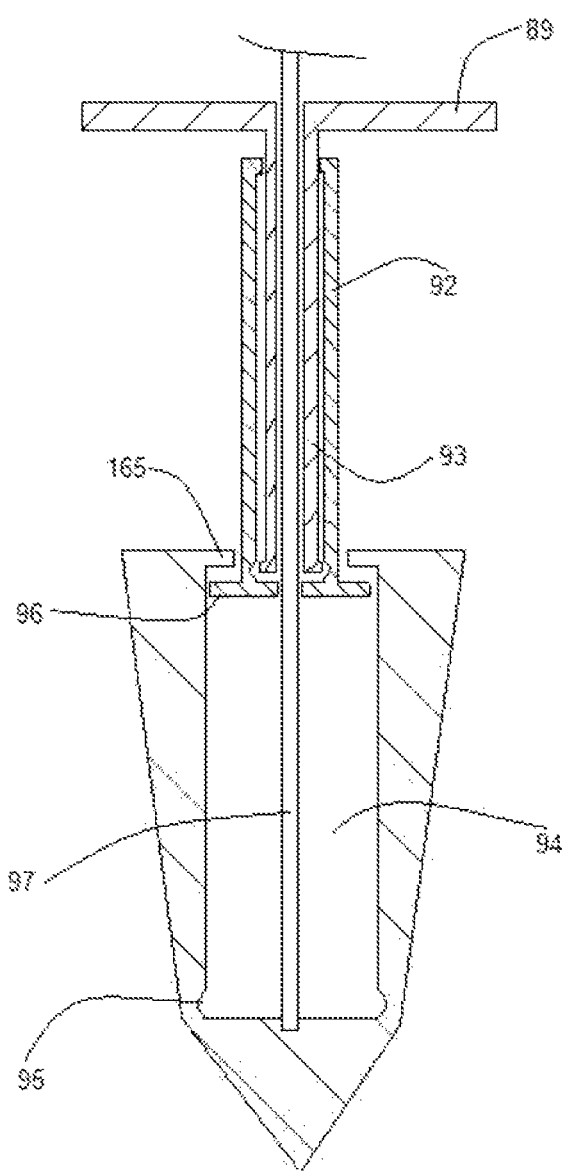
FIG. 34 is a cross-sectional side view of the screw in FIG. 33 shown in a partially extended position.
Figure 36:
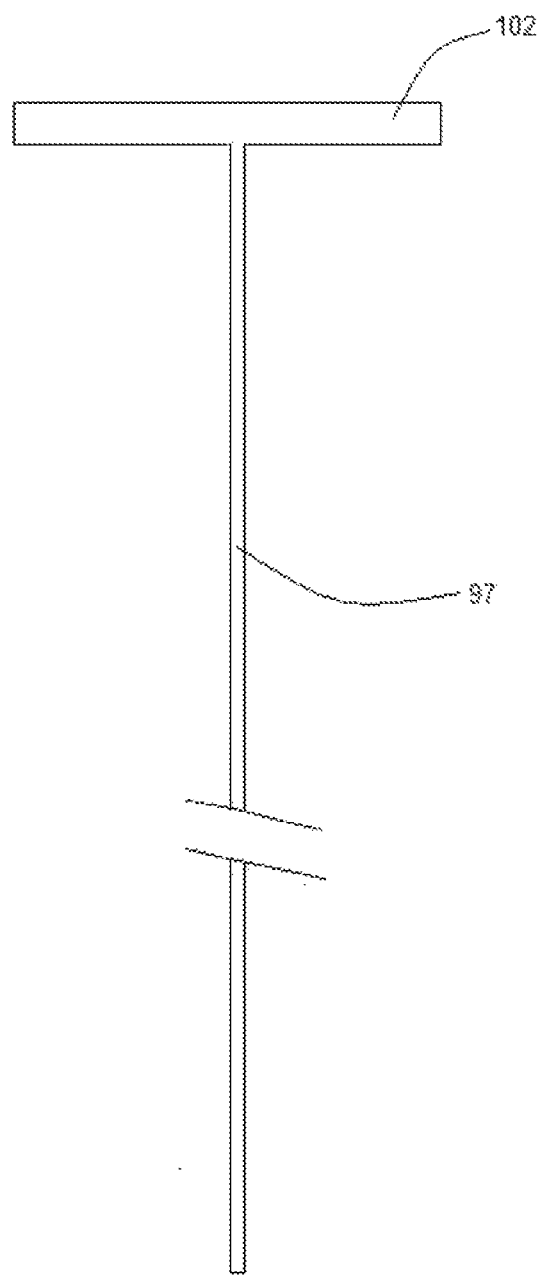
FIG. 36 is a side view of the screw driver used to place the screw shown in FIG. 33.
Figure 37:
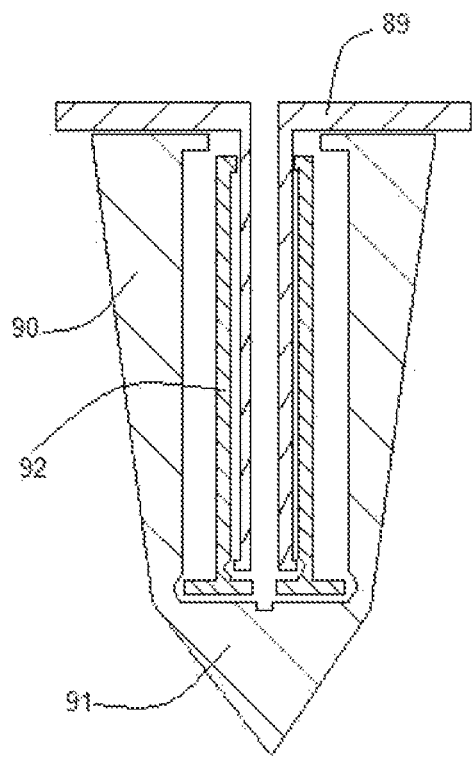
FIG. 37 is a cross-sectional side view of another embodiment of the telescopic screw in a retracted position.
Figure 38:
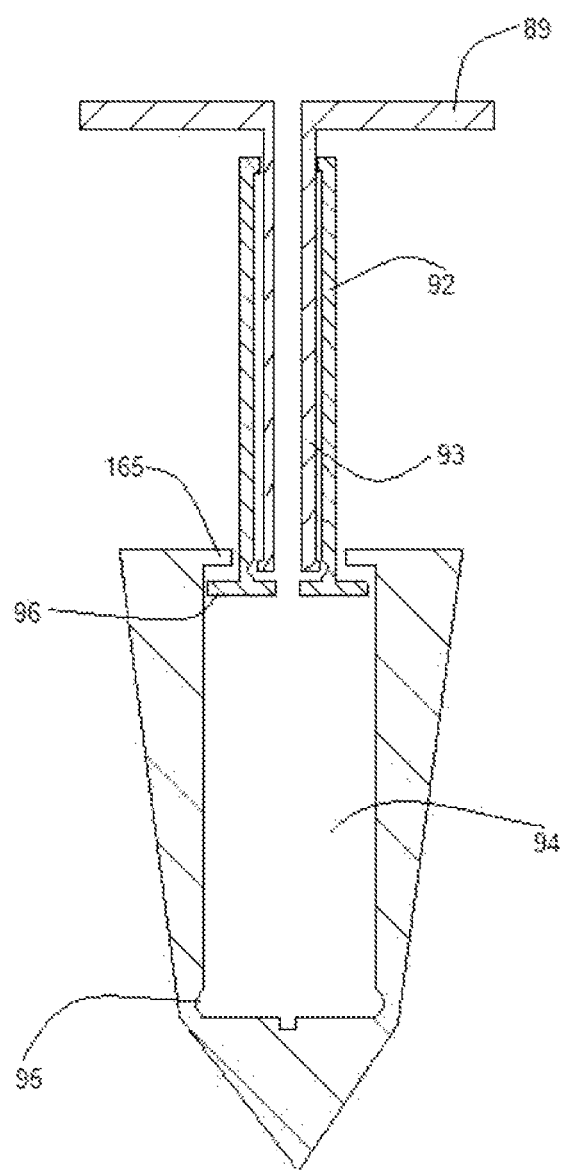
FIG. 38 is a cross-sectional side view of the screw in FIG. 37 shown in a partially extended position.
Figure 39:
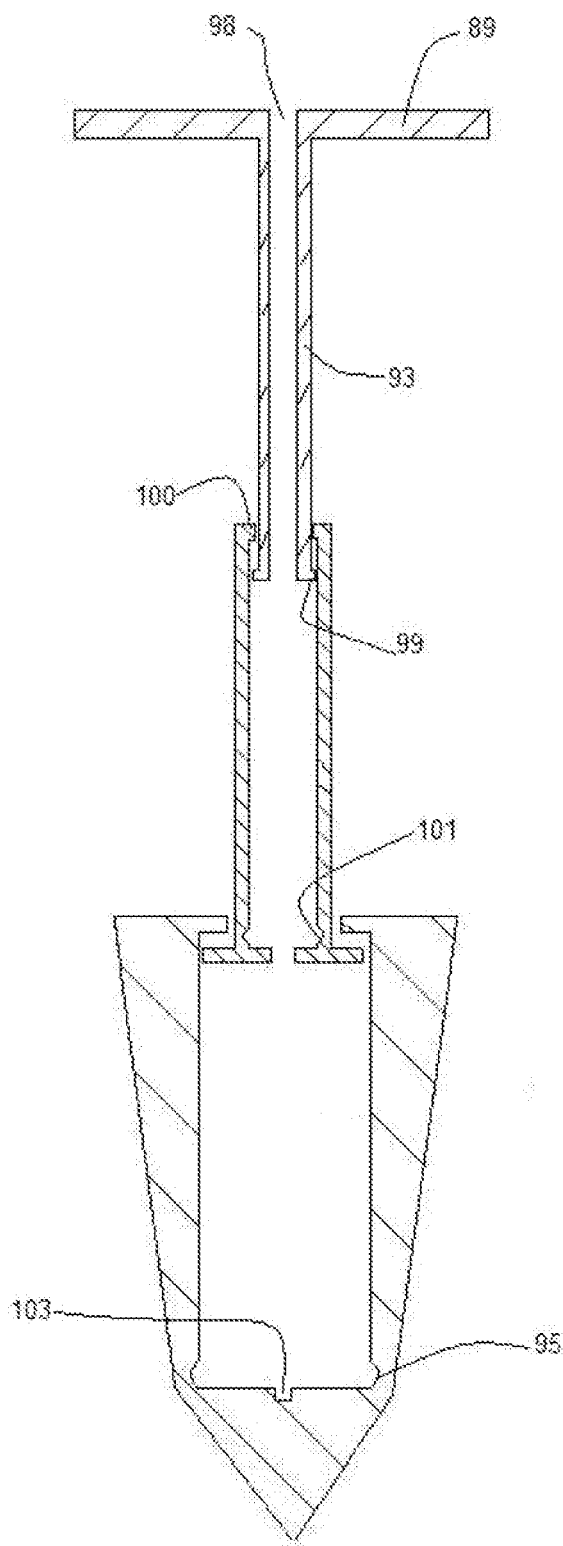
FIG. 39 is a cross-sectional side view of the screw in FIG. 37 shown in a completely extended position.

FIGS. 32-35 illustrate another embodiment of the telescopic screw with a housing component 90 containing a screw tip 91 and hollow center 94 with a recess 95 and extension 165 at the other end. The screw contains a telescopic component 93 with a head 89 at one end and extension 99 at the other end. The screw also contains an intermediate telescopic component 92 with an extension 96 on the outside at one end and recess 101 inside along with an extension 100 at the other end. In a retracted position of the screw as shown in FIG. 33 the intermediate telescopic component 92 is locked by engaging the extension 96 with the recess 95 and the telescopic component 93 is locked by engaging the extension 99 with the recess 101. FIG. 34 shows the screw in a partially extended position with the intermediate telescopic portion 92 in an extended position and the telescopic component 93 in a retracted position. The intermediate component extension 96 and the housing component extension 165 prevent the telescopic components from pulling out of the housing component. FIG. 35 shows the screw in a completely extended position with extensions 99 and 100 preventing the telescopic component from pulling out from the intermediate component. The screw also contains a central hollow component 98 for a screw driver shaft 97. FIG. 32 shows the top view of the screw head 89 with the hollow central portion 98. As shown in FIGS. 33-35 the screwdriver can be placed in a completely retracted, partially extended, or completely extended screw positions. FIG. 36 illustrates the screw driver with a shaft 97 and a head 102. FIGS. 37-39 illustrate the screw without the screwdriver in place.

FIGS. 40-43 illustrate another embodiment of the screw driver with a housing component 106 containing a screw tip 107, a hollow component 112 with a recess 111 and extension 117. The screw also contains a telescopic component 110 and an intermediate component 109. The telescopic component 110 comprises of a head 104 at one end and extension 114 at the other end. The intermediate component 109 is hollow and comprises of an extension 113 on the outside and recess 115 on the inside and extension 116 at the other end. The telescopic screw head 104 also contains holes 105 with corresponding recesses 108 in the housing component for the screw driver shafts. The screw driver as shown in FIG. 44 contains several shafts 119 and a head 118 and allows placement of the screw in retracted or extended positions. FIG. 40 shows the screw in a completely retracted position with locking mechanisms engaged. FIG. 41 shows the top view of the screw head 104 with holes 105 for the screwdriver shafts. FIG. 42 illustrates the screw driver in a partially extended position and FIG. 43 shows the screw in a completely extended position.

Figure 45:
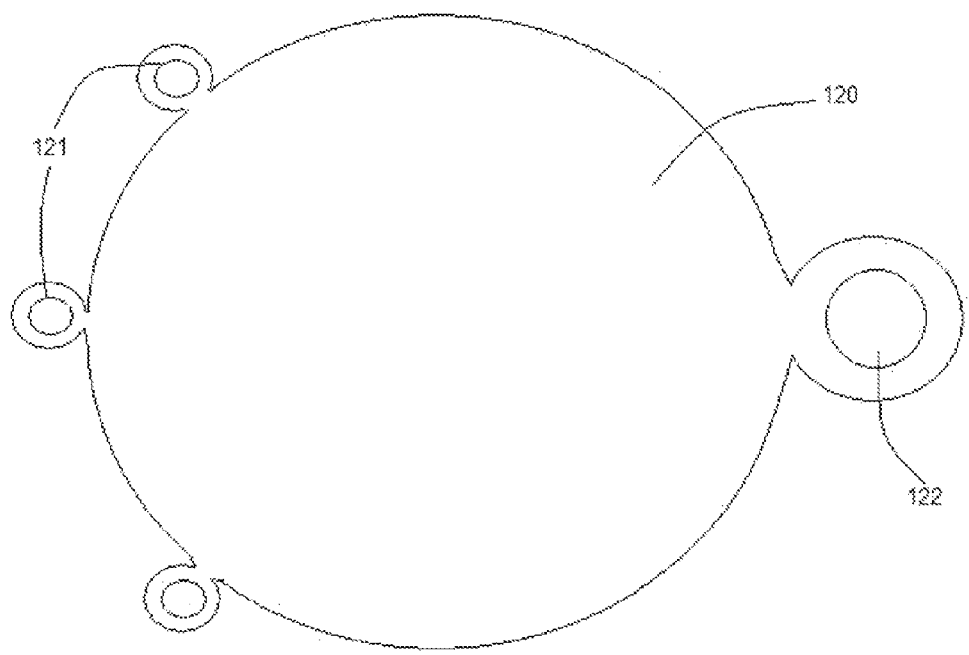
FIG. 45 is a top view of one embodiment of the cranial fixation plate.
Figure 46:
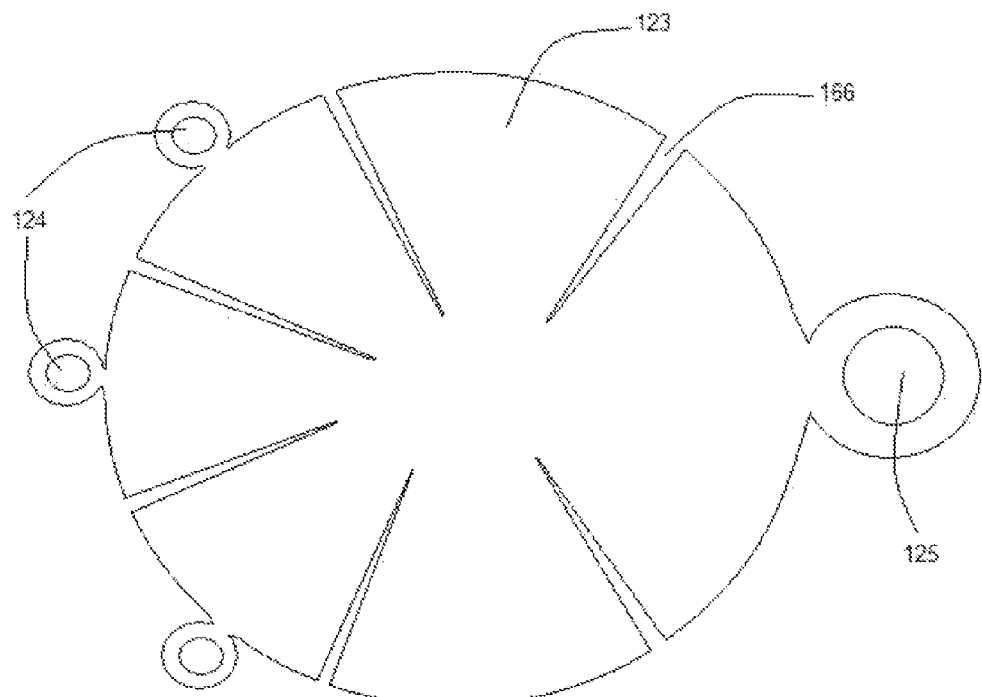
Figure 47:
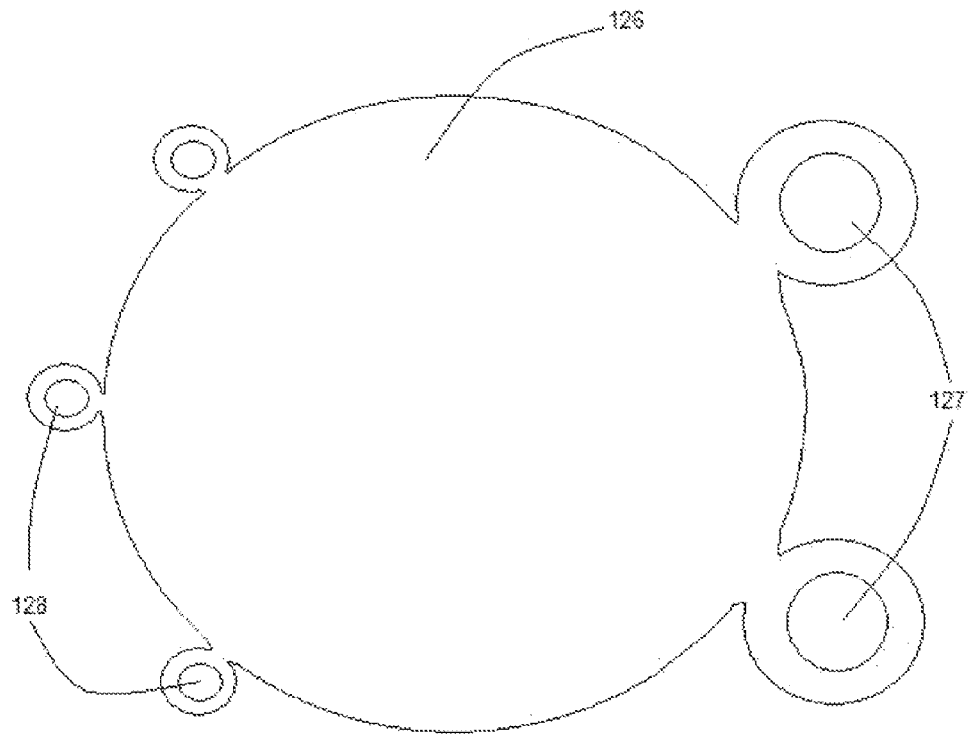
FIG. 47 is a top view of another embodiment of the cranial fixation plate.
Figure 48:
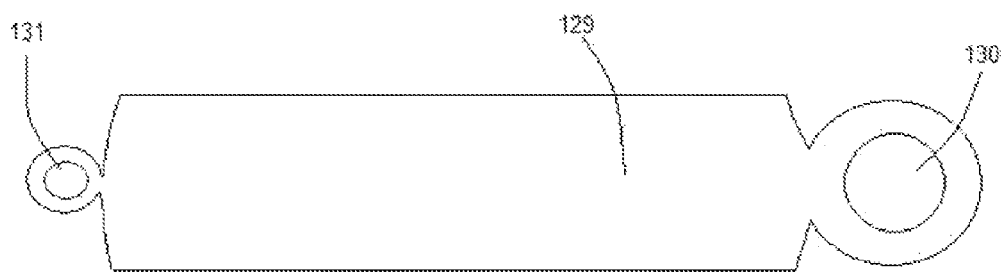
FIG. 48 is a top view of another embodiment of the cranial fixation plate.
Figure 49:
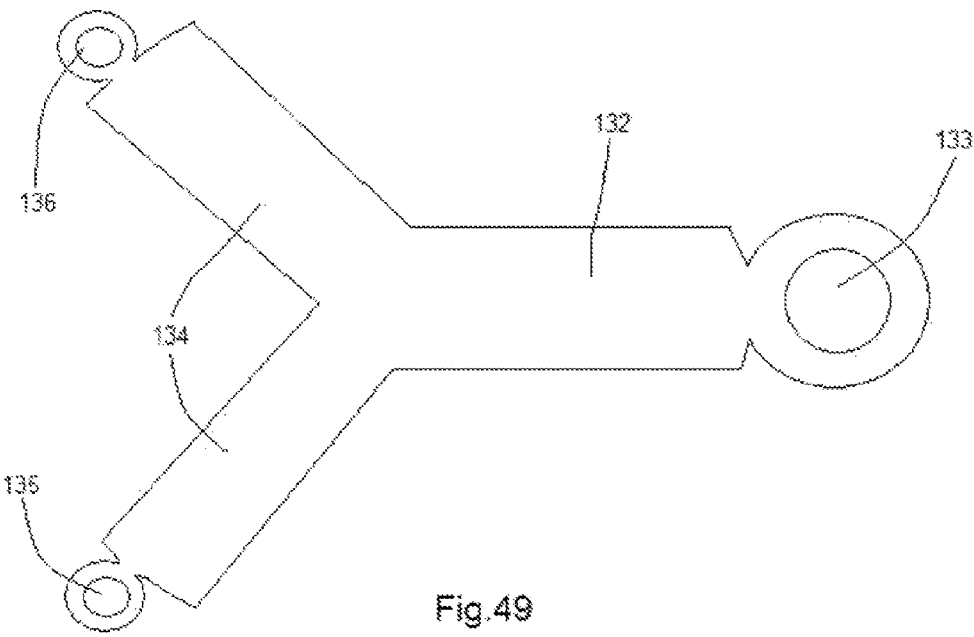
FIG. 49 is a top view of another embodiment of the cranial fixation plate.
Figure 50:
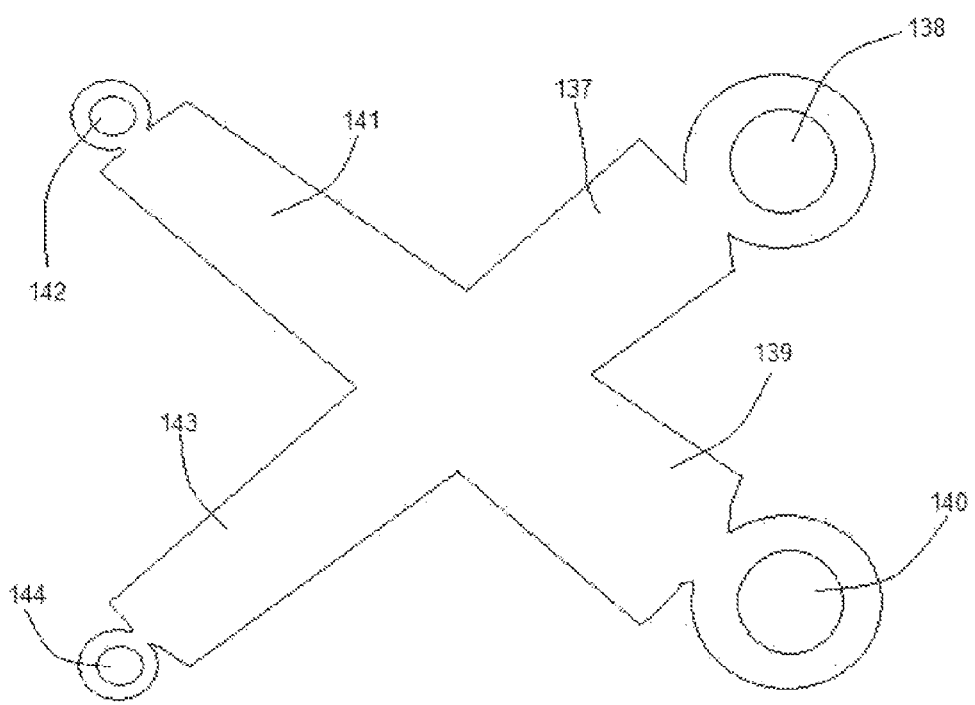
FIG. 50 is a top view of another embodiment of the cranial fixation plate.

FIG. 45 illustrates a round cranial plate 120 with holes 121 for regular screws and hole 122 for the telescopic screw. The telescopic screw has a larger diameter to accommodate the telescopic components and provide more structural strength. FIG. 46 illustrates a round plate 123 with recesses 166 to accommodate irregularities on the skull and bone flap surface. The plate also contains holes 124 for the regular screws and 125 for the telescopic screw. FIG. 47 illustrates a round cranial plate 126 with holes 128 for regular screws and holes 127 for the telescopic screws. FIG. 48 illustrates a straight plate 129 with a hole 131 for a regular screw and hole 130 for a telescopic screw. FIG. 49 illustrates a Y-Shape plate with extension 132 with telescopic screw hole 133 and extensions 134 for regular screw holes 135 and 136. FIG. 50 illustrates a X-Shape plate with extensions 137 and 139 with telescopic screw holes 138 and 140 and extensions 141 and 143 for regular screw holes 142 and 144. Other plate shapes can be rectangular or square.

Figure 51:
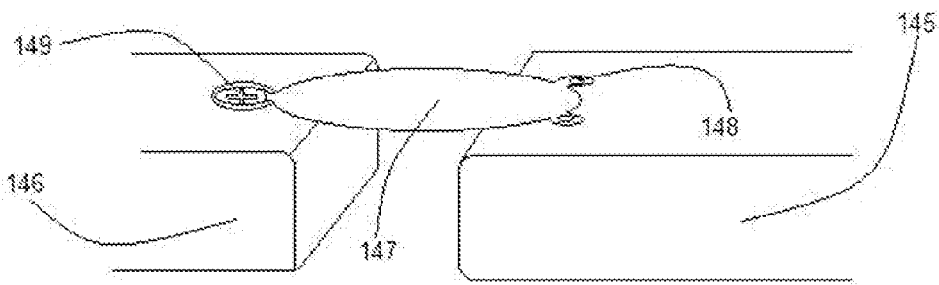
FIG. 51 is side plan view of one embodiment of the cranial plate attached to the bone flap and skull with the telescopic screw in a retracted position.
Figure 52:
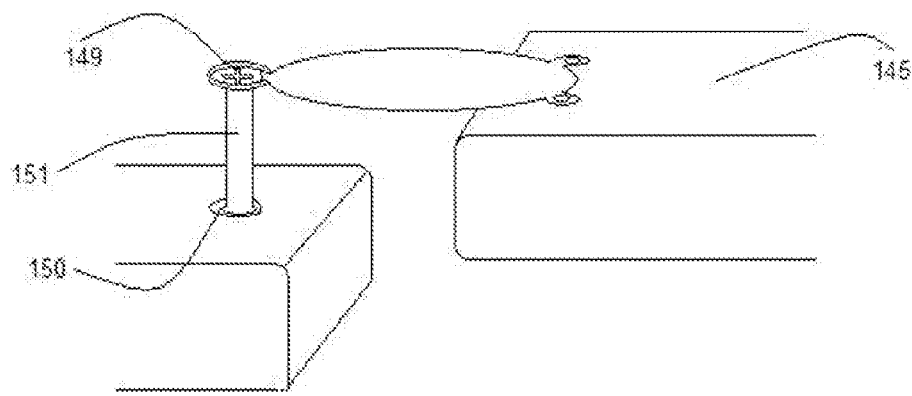
FIG. 52 is a side plan view of the plate in FIG. 51 with the telescopic screw in a partially extended position.
Figure 53:
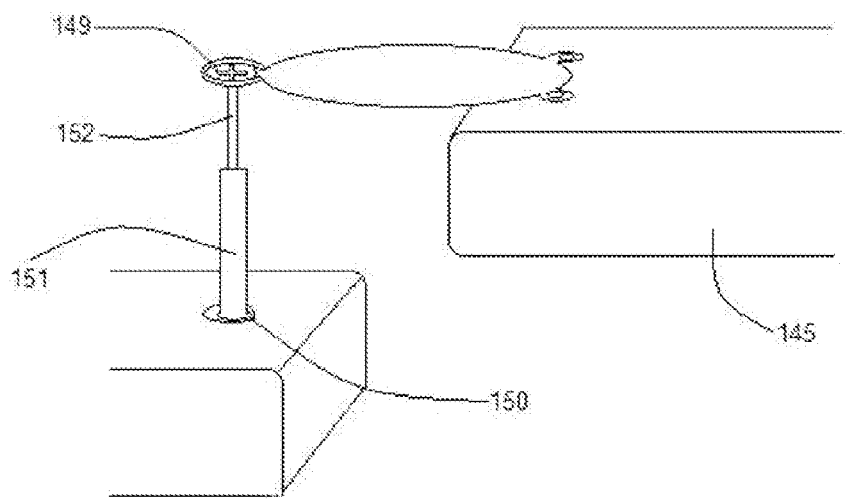
FIG. 53 is a side plan view of the plate in FIG. 51 with the telescopic screw in a completely extended position.

FIGS. 51-53 illustrate the constrained outward and inward movement of the bone flap relative to the skull allowed by the cranial fixation plate and telescopic screws. FIG. 51 illustrates the cranial fixation plate 147 attached to the bone flap 145 with regular screws 148 at one end and attached to the skull 146 with a telescopic screw 149. FIG. 52 illustrates the bone flap 145 pushed outwards by an increase in intracranial pressure with the telescopic screw 149 placed in a partially extended position with intermediate telescopic component 151 and housing component 150. FIG. 53 illustrates the telescopic screw 149 placed in a completely extended position allowing further outward movement of the bone flap 145 in response to further increase in intracranial pressure. The telescopic screw 149 is shown in complete extension with telescopic component 152, intermediate telescopic component 151 and housing component 150. With normalization of the intracranial pressure the pressure on the bone flap is relieved and the telescopic screws fall back into a retracted position approximating the bone flap to the skull.

Figure 54:
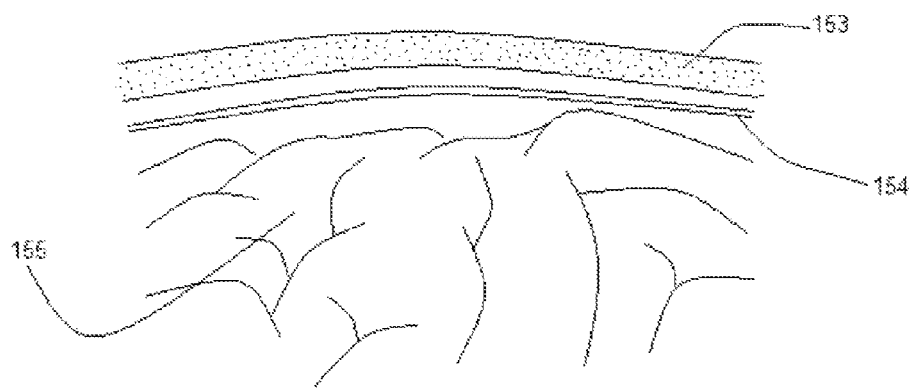
FIG. 54 is a partial cross-sectional side view of the skull and brain.
Figure 55:
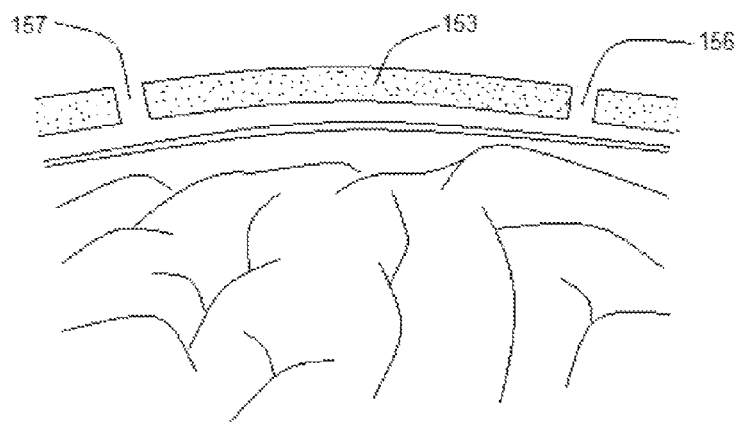
FIG. 55 is partial cross-sectional side view of the skull and brain.
Figure 56:
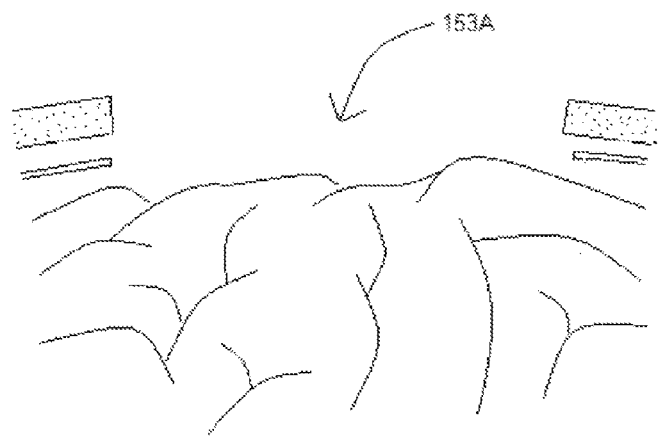
FIG. 56 is a partial cross-sectional side view of the skull and brain.
Figure 57:
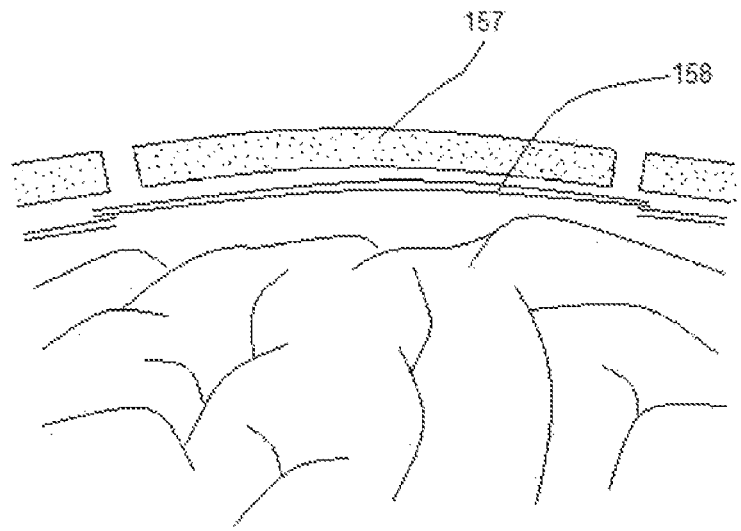
FIG. 57 is a partial cross-sectional side view of the skull and brain.
Figure 58:
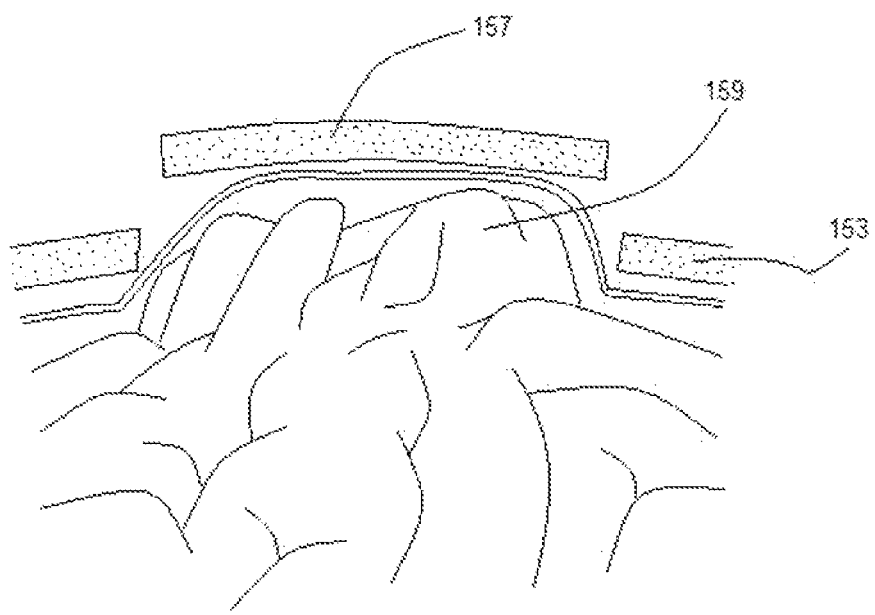
FIG. 58 is a partial cross-sectional side view of the skull and brain.
Figure 59:
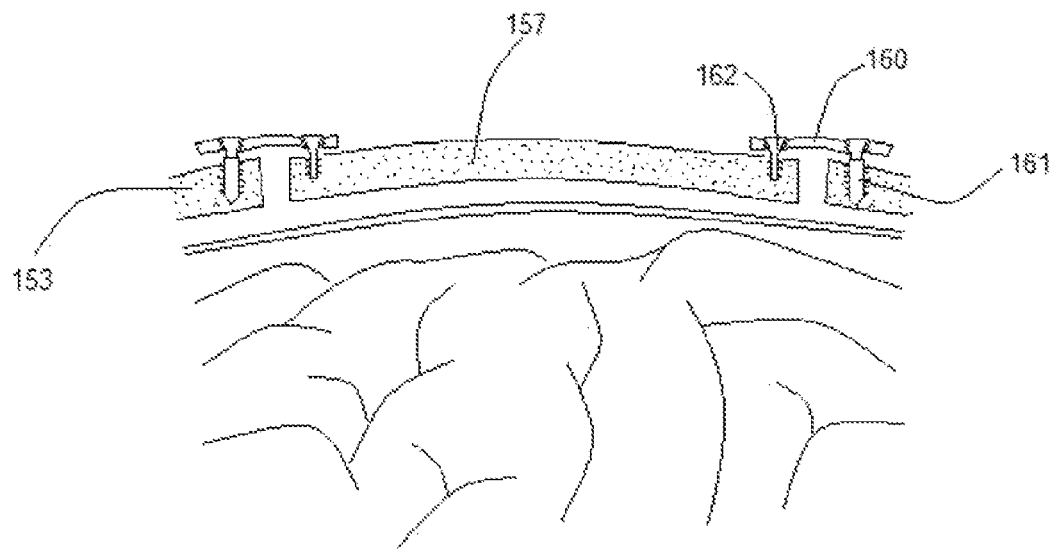
FIG. 59 is a partial cross-sectional side view of the skull and brain with cranial fixation plates and screws in place.
Figure 60:
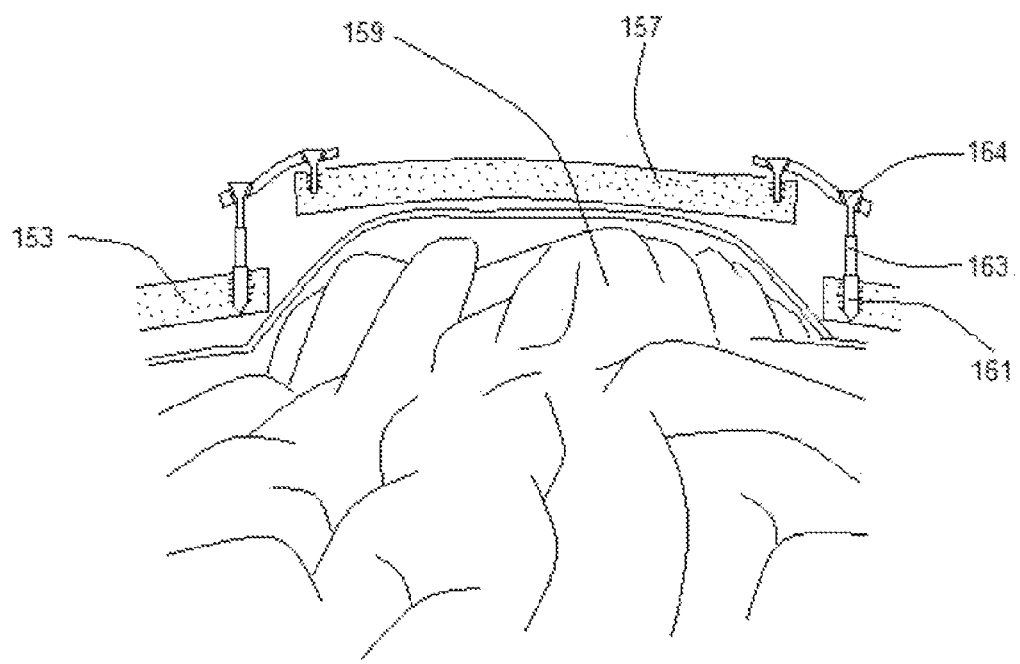
FIG. 60 is a partial cross-sectional side view of the skull and brain with cranial fixation plates and screws in place.

The constrained decompressive craniectomy methodology described in the current patent application is illustrated in FIGS. 54-60. FIG. 54 illustrates the brain 155, the dura 154, and the skull 153. FIG. 55 illustrates burr holes 156 and 156 created in the skull. FIG. 56 illustrates part of the skull (bone flap) 157 and dura removed. FIG. 57 illustrates the bone flap 157 replaced along with a dural patch graft 158 preferably made of an expandable synthetic collagen matrix. FIG. 58 illustrates the bone flap 157 pushed outwards relative to the skull 153 by the swollen brain 159 to accommodate the increase in intracranial pressure. FIG. 59 illustrates the bone flap 157 approximated to the skull 153 by cranial fixation plate 160 with regular screw 162 attached to the bone flap and telescopic screw 161 attached to the skull. FIG. 60 illustrates the swollen brain 159 compressing against the bone flap 157. The telescopic screw 161 contains the intermediate telescopic component 163 and telescopic head 164 and is placed in an extended position to allow the outward movement of the bone flap 157 relative to the skull 153. With resolution of the brain swelling the bone flap moves back inwards and the telescopic screws are placed in a retracted position. In case of severe brain swelling, the bone flap cannot be approximated to the skull until the swelling subsides. Placement of the cranial fixation plate requires the telescopic screw to be placed in an extended position. Alternatively, the telescopic screw housing component can be placed into the skull and the telescopic head can be placed after the plate as shown in FIGS. 61-68. FIGS.

Figure 61:
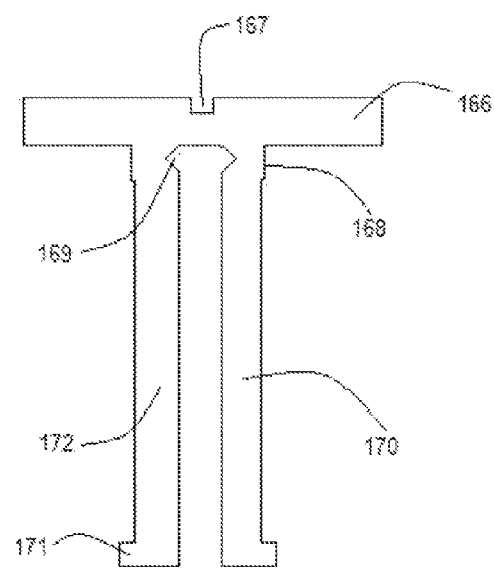
FIG. 61 is a side view of another embodiment of the telescopic extension.
Figure 62:
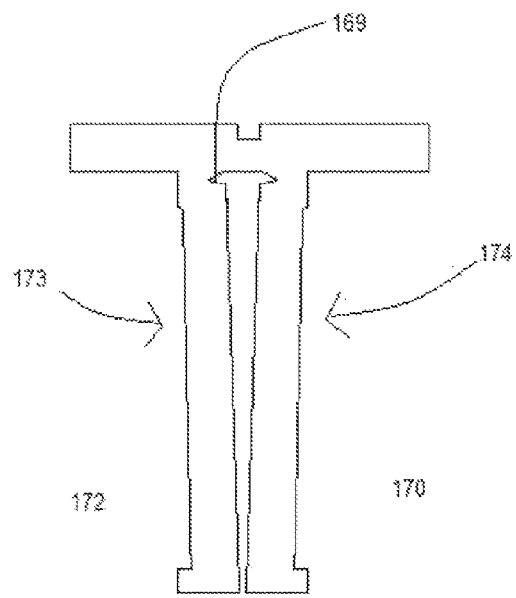
FIG. 62 is another side view of the telescopic extension seen in FIG. 61.
Figure 63:
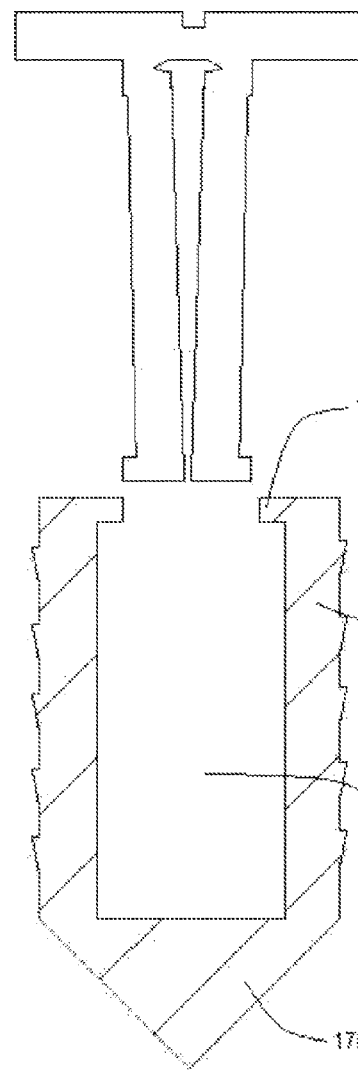
FIG. 63 is a cross-sectional side view of a telescopic housing member with the telescopic extension seen in FIG. 62 positioned outside the housing member.
Figure 64:
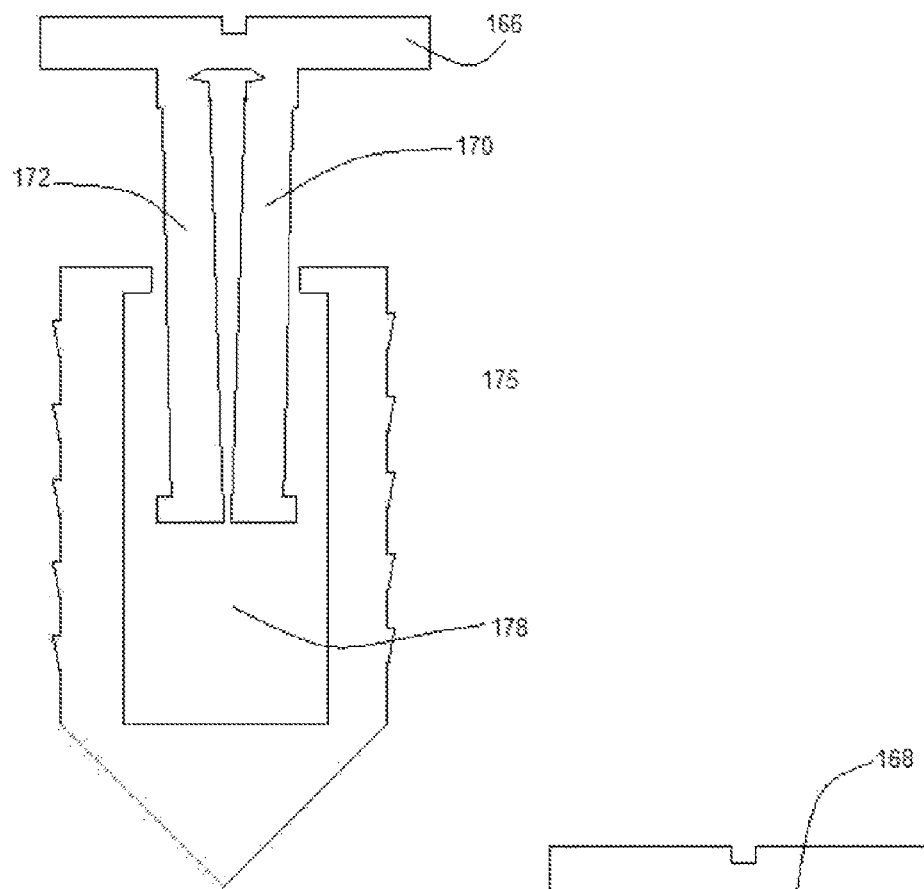
FIG. 64 is a cross-sectional side view of a telescopic housing member with the telescopic extension seen in FIG. 62 positioned inside the housing member.
Figure 65:
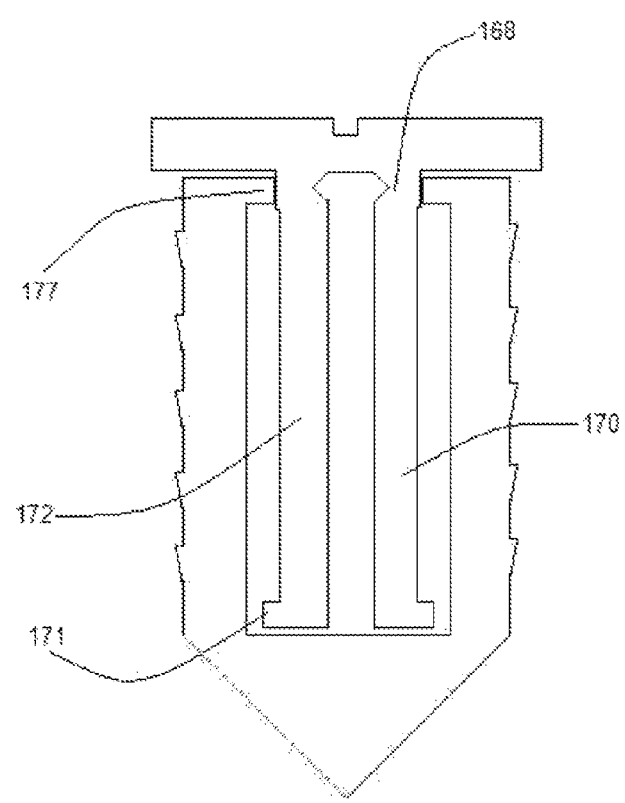
FIG. 65 is a cross-sectional side view of a telescopic housing member with the telescopic extension seen in FIG. 61 in a completely retracted position.
Figure 66:
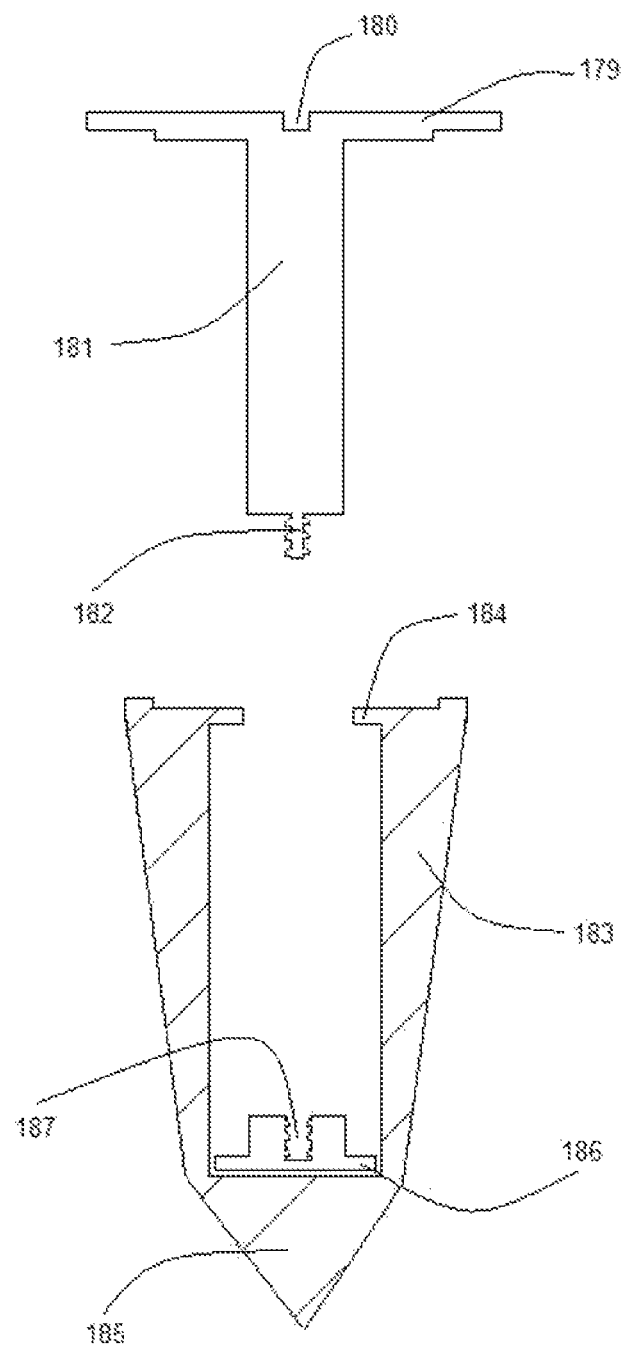
FIG. 66 is a partial cross-sectional side view of another embodiment of the telescopic screw.
Figure 67:
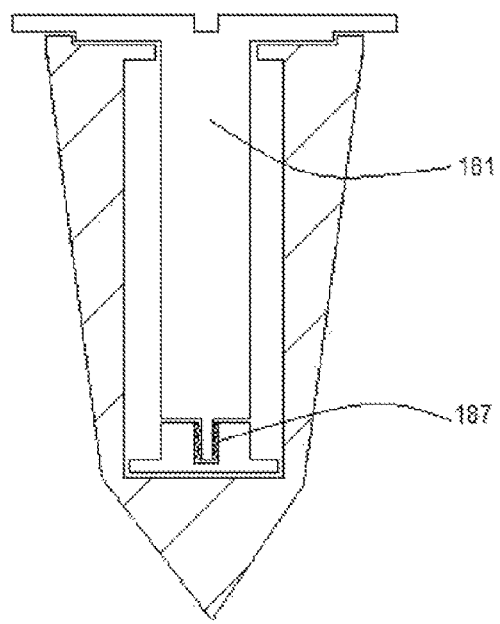
FIG. 67 is a partial cross-sectional side view of the screw in FIG. 67 in a retracted position.
Figure 68:
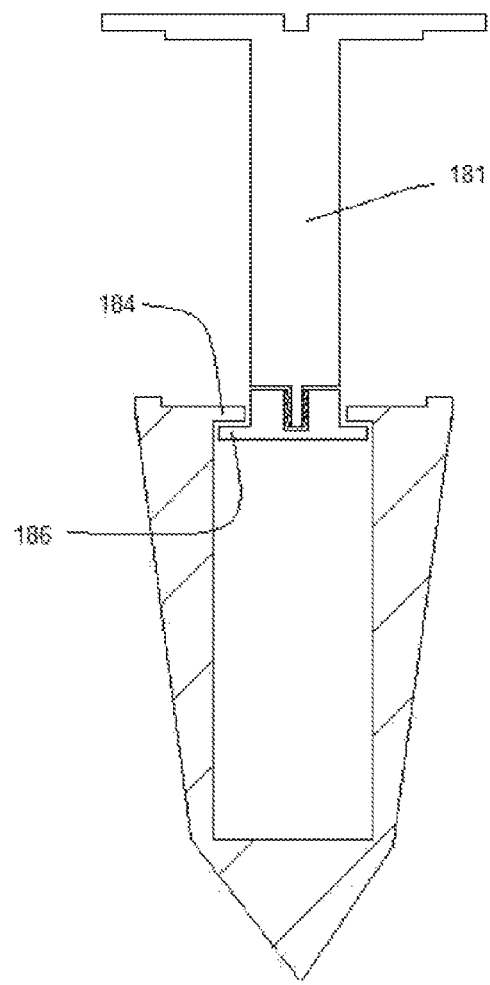
FIG. 68 is a partial cross-sectional view of the screw in FIG. 67 in an extended position.

61-65 illustrate one embodiment of the telescopic screw. The telescopic component as shown in FIG. 61 comprises of a head 166 with a recess 167 for the screw driver, extensions 170 and 172 with a proximal wider portion 168 on the outside and recesses 169 on the inside with distal extensions 171. As shown in FIG. 62 the extensions 170 and 172 can be compressed together manually 173 and 174 or with an instrument. The recesses 169 allow the extensions 170 and 172 to be compressed together thereby enabling the telescopic component to be placed after the housing component is implanted as shown in FIG. 63. The housing component 175 comprises of a screw tip 176, a hollow portion 178 and extension 177. As shown in FIG. 64 the telescopic component 166 is placed in the hollow portion 178 of the housing component 175 with the telescopic extensions 170 and 172 compressed. As shown in FIG. 65, the telescopic extensions 170 and 172 resume their normal positions after the compression is relieved. The extensions 171 on the telescopic component and the extension 177 on the housing component prevent the telescopic portion from pulling out from the housing component. The expanded portion 168 of the telescopic extensions engage with the extension 177 when the screw is in a retracted position. FIGS. 66-68 illustrate another embodiment of the telescopic screw. As shown in FIG. 66 the screw contains a telescopic component with a head 179, recess 180, body 181 and an engaging tip 182. The screw also contains a housing component with a body 183, tip 185, extension 184 and a telescopic slide component with an engaging recess 187 and extension 186. FIG. 67 illustrates the telescopic component 181 engaged with the telescopic slide component 187 in a retracted position. FIG. 68 illustrates the telescopic component 181 in an extended position. The extensions 184 and 186 prevent the telescopic component from pulling out of the housing component.

The cranial fixation device can be made of titanium or titanium alloy for MRI imaging compatibility. Other construction materials can include cobalt based alloys, cobalt-chrome alloys, cobalt-chromium-molybdenium, stainless steel alloys, ceramics and polymers. It could also be made of a bio-absorbable material (polyesters, poly amino acids, polyanhydrides, polyorthoesters, polyurethanes, polycarbonates, homopolymers, copolymers of poly lactic acid and poly glycolic acid, copolyesters of e-caprolactone, trimethylene carbonate, and para-dioxanone), or allograft or xenograft bone that is absorbed by the body over time once the bone flap has fused with the skull. Alternatively, it could be made of a radiolucent material like polyetheretherketone (PEEK) or polyaryletherketone (PEAK), high molecular weight polyethylene, carbon fiber, plastic, or a combination of plastic and metal to reduce CT and MRI imaging artifact. The cranial fixation device discussed herein can be of unitary construction and integral or formed of non-integral components attached together.

While the invention and methodology described herein along with the illustrations is specific, it is understood that the invention is not limited to the embodiments disclosed. Numerous modifications, rearrangements, and substitutions can be made with those skilled in the art without departing from the spirit of the invention as set forth and defined herein.

The invention claimed is:

1. A method of cranial fixation comprising the following steps:
attaching one or more plates to a skull and a bone flap with one or more bone fasteners, the one or more bone fasteners comprising non-telescoping screws and at least one telescoping bone fastener member, the at least one telescoping bone fastener member including a substantially hollow housing component further having an exterior wall and an interior wall, the interior wall adapted to receive an intermediate telescopic component and a telescopic component, the substantially hollow housing component including at a top end first extensions, wherein the first extensions prevent the intermediate telescopic component from pulling out of the substantially hollow housing component, the intermediate telescopic component including second extensions to prevent the telescopic component from pulling out of the intermediate telescopic component, and wherein each of the one or more plates includes a first set of holes at a first end of the plate and a larger second hole at a second end of the plate, the first set of holes and the larger second hole positioned as extensions from circular edges of the plate,
inserting the non-telescoping screws through the first set of holes of one of the one or more plates to attach the first end of the plate to the bone flap,
inserting one of the at least one telescoping bone fastener member through the larger second hole of the plate and inserting the substantially hollow housing component into the skull to attach the second end of the plate to the skull;
wherein the at least one telescoping bone fastener member allows the bone flap to approximate the skull when the at least one telescoping bone fastener member is in a retracted position.

2. The method of claim 1 including the further step of the bone flap moving outwardly by extension of the telescopic component to accommodate an increase in intracranial pressure.

3. The method of claim 2, wherein the increase in the intracranial pressure is from one or more of the following: traumatic injury subdural hemorrhage, epidural hemorrhage, subarachnoid hemorrhage, intra-ventricular hemorrhage, brain hemorrhage, ischemic stroke, hemorrhagic stroke, hypoxia, tumor, infection, brain swelling, and seizure.

4. The method of claim 1 including the further step of the bone flap moving inwardly by retraction of the telescopic component to accommodate a decrease in intracranial pressure.

5. The method o f claim 1 including the further step of the one or more bone fasteners anatomically approximating the skull and the bone flap when intracranial pressure normalizes.

6. The method of claim 1, wherein each of the one or more bone fasteners is selected from the group consisting of: screws, self-tapping screws, self-drilling screws, pins, rivets, wires, and sutures.

7. A method of cranial fixation comprising the following steps:
attaching one or more plates to a skull and a bone flap with one or more bone fasteners, the one or more bone fasteners comprising non-telescoping screws and at least one telescoping bone fastener, the at least one telescoping bone fastener including an essentially hollow housing component further having an exterior wall and an interior wall, the interior wall adapted to accept an intermediate telescopic component and a telescopic component and further comprising a locking mechanism, the essentially hollow housing component including at a top end first extensions, wherein the first extensions prevent the intermediate telescopic component from pulling out of the essentially hollow housing component, the intermediate telescopic component including second extensions to prevent the telescopic component from pulling out of the intermediate telescopic component, and wherein each of the one or more plates includes a first set of holes at a first end of the plate and a larger second hole at a second end of the plate, the first set of holes and the larger second hole positioned as circular extensions from edges of the plate, inserting the non-telescoping screws through the first set of holes of one of the one or more plates to attach the first end of the plate to the bone flap, inserting one of the at least one telescoping bone fastener through the larger second hole of the plate and inserting the essentially hollow housing component into the skull to attach the second end of the plate to the skull;

wherein the at least one telescoping bone fastener allows the bone flap to approximate the skull when intracranial pressure normalizes.

8. The method of claim 7, including the further step of the locking mechanism engaging when the at least one telescoping bone fastener is in a retracted state.

9. The method of claim 7, wherein the locking mechanism is selected from the group consisting of: ball and socket, collapsible ball and socket, ratchet teeth, collapsible ratchet teeth, ridges, hook, threads, spring, hooks, clips, and ridge and socket.

10. The method of claim 7 including the further step of the locking mechanism disengaging when there is an increase in intracranial pressure.

11. The method of claim 10, wherein the increase in the intracranial pressure is from one or more of the following: traumatic injury, subdural hemorrhage, epidural hemorrhage, subarachnoid hemorrhage, intra-ventricular hemorrhage, brain hemorrhage, ischemic stroke, hemorrhagic stroke, hypoxia, tumor, infection, brain swelling, and seizure.

12. The method of claim 7, wherein each of the one or more plates has a configuration selected from the group consisting of: round, oval, rectangular, square, half round, half oval, X-shape, Y-shape, and fan-shaped.

* * * * *